United States Patent [19]

Fujikawa et al.

[11] Patent Number: 5,024,999

[45] Date of Patent: Jun. 18, 1991

[54] PYRAZOLOPYRIDINE TYPE MEVALONOLACTONES USEFUL AS PHARMAEUTICALS

[75] Inventors: Yoshihiro Fujikawa; Mikio Suzuki; Hiroshi Iwasaki, all of Funabashi; Mitsuaki Sakashita; Masaki Kirahara, both of Shiroaoka, all of Japan

[73] Assignee: Nissan Chemical Industries Ltd., Tokyo, Japan

[21] Appl. No.: 337,411

[22] Filed: Apr. 13, 1989

[30] Foreign Application Priority Data

Apr. 26, 1988 [JP] Japan .................. 63-103090
Oct. 27, 1988 [JP] Japan .................. 63-271439
Jan. 26, 1989 [JP] Japan .................... 1-16846
Apr. 7, 1989 [JP] Japan .................... 1-88534

[51] Int. Cl.$^5$ .................. A61K 31/435; C07D 471/04
[52] U.S. Cl. ..................... 514/63; 514/278; 514/303; 546/14; 546/15; 546/119
[58] Field of Search .............. 546/119, 14, 15; 514/303, 63, 278

[56] References Cited

U.S. PATENT DOCUMENTS 4,761,419 8/1988 Picard et al. .................. 514/311
4,822,799 4/1989 Kathawala et al. ............. 546/119

FOREIGN PATENT DOCUMENTS 114027 7/1984 European Pat. Off. .
327500 8/1989 European Pat. Off. .
84/02131 6/1984 PCT Int'l Appl. .
8600307 1/1986 World Int. Prop. O. .

*Primary Examiner*—Bernard Dentz
*Attorney, Agent, or Firm*—Oblon, Spivak, McClelland, Maier & Neustadt

[57] ABSTRACT

The present invention provides a compound of the formula:

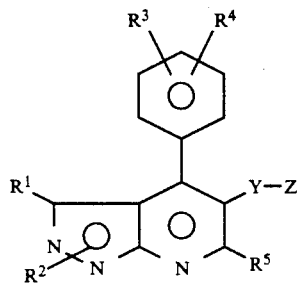

process for their production, pharmaceutical compositions containing them and their pharmaceutical uses, and intermediates useful for their production and processes for the production of such intermediates.

22 Claims, No Drawings

PYRAZOLOPYRIDINE TYPE MEVALONOLACTONES USEFUL AS PHARMAEUTICALS

The present invention relates to novel mevalonolactones having a pyrazolopyridine ring, processes for their production, pharmaceutical compositions containing them and their pharmaceutical uses particularly as anti-hyperlipidemic, hypolipoproteinemic and anti-atherosclerotic agents, and intermediates useful for their production and processes for the production of such intermediates.

Some fermentation metabolic products such as compactin, CS-514, Mevinolin or semi-synthetic derivatives or fully synthetic derivatives thereof are known to be inhibitors against HMG-CoA reductase which is a rate limiting enzyme for cholesterol biosynthesis. (A. Endo J. Med Chem., 28(4) 401 (1985))

CS-514 and Mevinolin have been clinically proved to be potentially useful anti-hyperlipoproteinemic agents, and they are considered to be effective for curing or preventing diseases of coronary arteriosclerosis or atherosclerosis. (IXth Int. Symp. Drugs Affect. Lipid Metab., 1986, p30, p31, p66)

However, with respect to fully synthetic derivatives, particularly hetero aromatic derivatives of inhibitors against HMG-CoA reductase, limited information is disclosed in the following literatures:

WPI ACC No. 84-157675, 86-028274, 86-098816, 86-332070, 87-124519, 87-220987, 88-07781, 88-008460, 88-091798, 88-112505, 88-182950, 88-205067, 88-234828, 88-258359 and 88-300969.

The present inventors have found that mevalonolactone derivatives having a pyrazolopyridine ring, the corresponding dihydroxy carboxylic acids and salts and esters thereof have high inhibitory activities against cholesterol biosynthesis wherein HMG-CoA reductase acts as a rate limiting enzyme The present invention has been accomplished on the basis of this discovery.

The novel mevalonolactone derivatives of the present invention are represented by the following formula I:

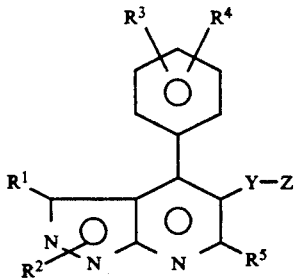

(I)

wherein $R^1$ is hydrogen, $C_{1-8}$ alkyl, $C_{1-6}$ alkoxy, $C_{3-7}$ cycloalkyl, $C_{2-6}$ alkenyl, α- or β-naphthyl, 2-, 3- or 4-pyridyl, 2- or 3-thienyl, 2- or 3-furyl, fluoro, chloro, bromo,

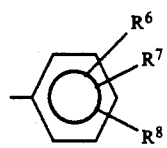

(wherein $R^6$, $R^7$ and $R^8$ are independently hydrogen, $C_{1-8}$ alkyl, $C_{1-8}$ alkoxy, $C_{1-3}$ alkylthio, chloro, bromo, fluoro, —$NR^9R^{10}$ (wherein $R^9$ and $R^{10}$ are independently $C_{1-3}$ alkyl), chloromethyl, trichloromethyl, trifluoromethyl, trifluoromethoxy, trichloromethoxy, difluoromethoxy, phenoxy, benzyloxy, hydroxy, trimethylsilyloxy, diphenyl-t-butylsilyloxy, hydroxymethyl or —$O(CH_2)_kOR^{18}$ (wherein $R^{18}$ is hydrogen or $C_{1-3}$ alkyl, and k is 1, 2 or 3); when $R^8$ is hydrogen and when located at the ortho position to each other, $R^6$ and $R^7$ may together form —$OC(R^{19})(R^{20})O$— (wherein $R^{19}$ and $R^{20}$ are independently hydrogen or $C_{1-3}$ alkyl); or when $R^7$ and $R^8$ are hydrogen at the same time, $R^6$ is

(wherein $R^{25}$ is hydrogen, $C_{1-4}$ alkyl, $C_{1-3}$ alkoxy, trifluoromethyl, chloro, bromo, or fluoro)), phenyl-$C_{2-3}$ alkenyl of which the phenyl group is unsubstituted or substituted by $C_{1-4}$ alkyl, $C_{1-3}$ alkoxy, fluorine, chlorine or bromine, or $C_{1-3}$ alkyl substituted by one member selected from the group consisting of $C_{1-3}$ alkoxy, naphthyl and

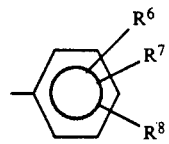

(wherein $R^6$, $R^7$ and $R^8$ are as defined above); $R^2$ is bonded to nitrogen at the 1- or 2-position of the pyrazolopyridine ring and is hydrogen, $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl, 2- or 3-thienyl, 2- or 3-furyl or

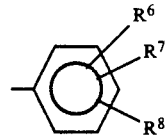

(wherein $R^6$, $R^7$ and $R^8$ are as defined above), or $C_{1-3}$ alkyl substituted by one member selected from the group consisting of $C_{1-3}$ alkoxy, hydroxy, naphthyl and

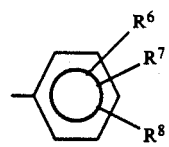

(wherein $R^6$, $R^7$ and $R^8$ are as defined above); $R^3$ and $R^4$ are independently hydrogen, $C_{1-8}$ alkyl, $C_{3-7}$ cycloalkyl, $C_{1-3}$ alkoxy, n-butoxy, i-butoxy, sec-butoxy, butoxy, $R^{23}R^{24}N$— (wherein $R^{23}$ and $R^{24}$ are independently hydrogen or $C_{1-3}$ alkyl), trifluorometyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —$O(CH_2)_iOR^{15}$ (wherein $R^{15}$ is hydrogen or $C_{1-3}$ alkyl, and $l$ is 1, 2 or 3); or when located at the ortho position to each other, $R^3$ and $R^4$ may together form —CH=CH—CH=CH— or methylene dioxy; Y is —CH$_2$—, —CH$_2$CH$_2$—, —CH=CH—, —CH$_2$—CH=CH—, —CH=CH—CH$_2$—, —C(CH$_3$)=CH— or —CH=C(CH$_3$); Z is —Q—CH$_2$WCH$_2$—CO$_2$R$^{12}$,

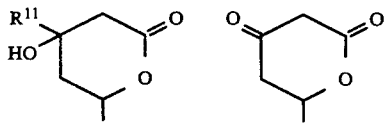

or

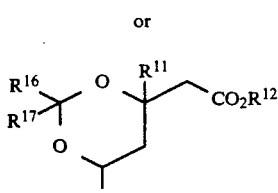

(wherein Q is —C(O)—, —C(OR$^{13}$)$_2$— or —CH(OH)—; W is—C(O)—, —C(OR$^{13}$)$_2$— or —C(R$^{11}$)(OH)—; $R^{11}$ is hydrogen or $C_{1-3}$ alkyl; $R^{12}$ is hydrogen or $R^{14}$ (wherein $R^{14}$ is alkyl moiety of chemically or physiologically hydrolyzable alkyl ester or M (wherein M is NH$_4$, sodium, potassium, ½ calcium or a hydrogen addition product to nitrogen of lower alkylamine, di-lower alkylamine or tri-lower alkylamine)): two $R^{13}$ are independently primary or secondary $C_{1-6}$ alkyl; or two $R^{13}$ together form —(CH$_2$)$_2$— or —(CH$_2$)$_3$—; $R^{16}$ and $R^{17}$ are independently hydrogen or $C_{1-3}$ alkyl; or $R^{16}$ and $R^{17}$ together form —(CH$_2$)$_2$— or —(CH$_2$)$_3$—; $R^5$ is hydrogen, chloro, bromo, hydroxy, $C_{1-3}$ alkoxy, $R^{23}R^{24}N$— (wherein $R^{23}$ and $R^{24}$ are independently hydrogen or $C_{1-3}$ alkyl), $C_{1-8}$ alkyl, $C_{2-6}$ alkenyl, $C_{3-7}$ cycloalkyl, $C_{5-7}$ cycloalkenyl, trifluoromethyl or

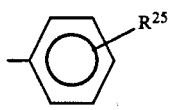

(wherein $R_{25}$ is as defined above), or $C^{1-3}$ alkyl substituted by one member selected from the group consisting of

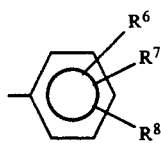

(wherein $R^6$, $R^7$ and $R^8$ are as defined above) and by 0, 1 or 2 members selected from the group consisting of $C_{1-3}$ alkyl.

Various substituents in the formula I will be described in detail with reference to specific examples. However, it should be understood that the present invention is by no means restricted by such specific examples.

$C_{1-8}$ alkyl for $R^1$, $R^2$, $R^3$, $R^4$, $R^5$, $R^6$, $R^7$ and $R^8$ includes, for example, methyl, ethyl, n-propyl, i-propyl, n-butyl, i-butyl, sec-butyl, t-butyl, n-pentyl, n-hexyl, n-heptyl and n octyl. $C_{3-7}$ cycloalkyl for $R^1$, $R^2$, $R^3$, $R^4$ and $R^5$ includes, for example, cyclopropyl, cyclobutyl, cyclopentyl, cyclohexyl, 4-methylcyclohexyl and cycloheptyl.

$C_{1-8}$ alkoxy for $R^6$, $R^7$ and $R^8$ includes, for example, methoxy, ethoxy, n-propoxy, i-propoxy, n-butoxy, n-pentoxy, n-hexyloxy, n-heptyloxy and n-octyloxy.

$C_{1-3}$ alkylthio for $R^6$, $R^7$ and $R^8$ includes, for example, methylthio, ethylthio, n-propylthio and i-propylthio.

$C_{1-3}$ alkyl for $R^9$ and $R^{10}$ includes, for example, methyl, ethyl, n-propyl and i-propyl.

$C_{1-3}$ alkyl for $R^{11}$ includes, for example, methyl, ethyl, n-propyl and i-propyl.

$C_{1-6}$ alkyl for $R^{13}$ includes, for example, methyl, ethyl, n-propyl, i-propyl, n-butyl, i butyl, sec-butyl, n-pentyl and n-hexyl.

$C_{1-3}$ alkyl for $R^{15}$, $R^{16}$, $R^{17}$, $R^{18}$, $R^{19}$, $R^{20}$, $R^{23}$ and $R^{24}$ includes, for example, methyl, ethyl, n-propyl and i-propyl.

$C_{1-4}$ alkyl for $R^{25}$ includes, for example, methyl, ethyl, n-propyl, i-propyl, n-butyl, i-butyl, sec-butyl and t-butyl.

Further, these compounds may have at least one or two asymmetric carbon atoms and may have at least two to four optical isomers. The compounds of the formula I include all of these optical isomers and all of the mixtures thereof.

Among compounds having carboxylic acid moieties falling outside the definition of —CO$_2$R$^{12}$ of the carboxylic acid moiety of substitutent Z of the compounds of the present invention, those which undergo physiological hydrolysis, after intake, to produce the corresponding carboxylic acids (compounds wherein the —CO$_2$R$^{12}$ moiety is —CO$_2$H) are equivalent to the compounds of the present invention.

Now, preferred substitutents of the compounds of the present invention will be described.

In the following preferred, more preferred, still further preferred and most preferred examples, the numerals for the positions of the substituents indicate the positions on the pyrazolopyridine ring.

Preferred examples for $R^1$ and $R^2$ are as defined with respect to the formula I.

As preferred examples for $R^3$ and $R^4$, when $R^4$ is hydrogen, $R^3$ is hydrogen, 3-fluoro, 3-chloro, 3-methyl, 4-methyl, 4-chloro or 4-fluoro; or $R^3$ and $R^4$ together form 3-methyl-4-chloro, 3,5-dichloro, 3,5-difluoro, 3,5-dimethyl or 3 methyl-4-fluoro.

Preferred examples for $R^5$ include primary and secondary $C_{1-6}$ alkyl and $C_{3-6}$ cycloalkyl.

Preferred examples for Y include —CH$_2$—CH$_2$— and —CH=CH—.

Preferred examples for Z include

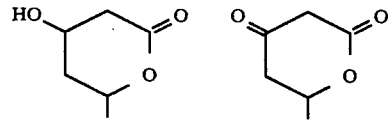

—CH(OH)CH$_2$CH(OH)CH$_2$CO$_2$R$^{12}$, —CH(OH)CH$_2$C(O)CH$_2$CO$_2$R$^{12}$ and —CH(OH)CH$_2$C(OR$^{13}$)$_2$CH$_2$CO$_2$R$^{12}$.

Now, more preferred substituents of the compounds of the present invention will be described.

More preferred examples for $R^1$ include hydrogen, $C_{1-8}$ alkyl, $C_{1-6}$ alkoxy, $C_{3-7}$ cycloalkyl, $C_{2-6}$ alkenyl, α- or β-naphthyl, 2-, 3- or 4-pyridyl, 2- or 3-thienyl, 2- or 3-furyl,

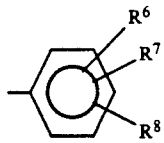

(wherein $R^6$, $R^7$ and $R^8$ are as defined above) and $C_{1-3}$ alkyl substituted by one member selected from the group consisting of $C_{1-3}$ alkoxy, naphthyl and

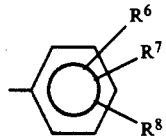

(wherein $R^6$, $R^7$ and $R^8$ are as defined above) and by 0, 1 or 2 members selected from the group consisting of $C_{1-8}$ alkyl.

As more preferred examples for $R^2$, when $R^2$ is bonded to nitrogen at the 1- or 2-position of the pyrazolopyridine ring, $R^2$ is $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl,

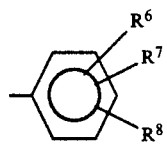

(wherein $R^6$, $R^7$ and $R^8$ are as defined above) and $C_{1-3}$ alkyl substituted by one member selected from the group consisting of $C_{1-3}$ alkoxy, hydroxy, naphthyl and

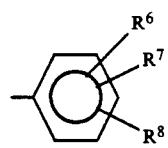

(wherein $R^6$, $R^7$ and $R^8$ are as defined above) and by 0, 1 or 2 members selected from the group consisting of $C_{1-8}$ alkyl.

As more preferred examples for $R^3$ and $R^4$, when $R^4$ is hydrogen, $R^3$ is hydrogen, 4-methyl, 4-chloro or 4-fluoro; or $R^3$ and $R^4$ together form 3,5-dimethyl or 3-methyl-4-fluoro.

More preferred examples for Y include —CH$_2$—CH$_2$— and (E)—CH=CH—.

Now, still further preferred substituents of the compounds of the present invention will be described.

Still further preferred examples for $R^1$ include hydrogen, $C_{1-8}$ alkyl, $C_{3-7}$ cycloalkyl, $C_{2-6}$ alkenyl and

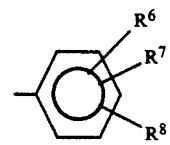

(wherein $R^6$, $R^7$ and $R^8$ are as defined above).

As still further preferred examples for $R^2$, when $R^2$ is bonded to nitrogen at the 1-position of the pyrazolopyridine ring, $R^2$ is $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl

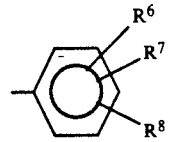

(wherein $R_6$, $R_7$ and $R_8$ are as defined above) and $C_{1-3}$ alkyl substituted by one member selected from the group consisting of $C_{1-3}$ alkoxy, hydroxy, naphthyl and

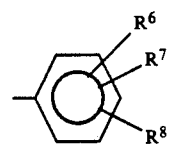

(wherein $R^6$, $R^7$ and $R^8$ are as defined above) and by 0, 1 or 2 members selected from the group consisting of $C_{1-8}$ alkyl.

As still further preferred examples for $R^2$, when $R^2$ is bonded to nitrogen at the 2-position of the pyrazolopyridine ring, $R^2$ is α- or β-naphthyl and

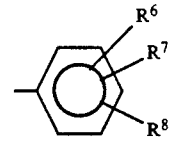

(wherein $R^6$, $R^7$ and $R^8$ are as defined above).

As still further preferred examples for $R^3$ and $R^4$, when $R^4$ is hydrogen, $R^3$ is hydrogen, 4-chloro or 4-fluoro; or $R^4$ and $R^3$ together form 3-methyl-4-fluoro.

Still further preferred examples for $R^5$ include ethyl, n-propyl, i-propyl and cyclopropyl.

Still further preferred example for Y includes (E)—-CH=CH—.

Now, the most preferred substituents for the compounds of the present invention will be described.

The most preferred examples for $R^1$ include hydrogen, methyl, ethyl, n-propyl, i-propyl, n-butyl, i-butyl, sec-butyl, t-butyl, cyclopropyl, cyclohexyl, phenyl, 2-, 3- or 4-fluorophenyl, 2-, 3- or 4-chlorophenyl, 2-, 3- or 4-bromophenyl, 2-, 3- or 4-tolyl, 2-, 3- or 4-methoxyphenyl, 2-, 3- or 4-trifluoromethylphenyl, 2-, 3- or 4-chloromethylphenyl, 3- or 4-ethoxyphenyl, 4-(2-methylbutyl)phenyl, 4-n-heptylphenyl, 4-n-octylphenyl, 4-n-pentylphenyl, 4-n-hexylphenyl, 4-n-propylphenyl, 4-n-butylphenyl, 4-t-butylphenyl, 4-n-butoxyphenyl, 4-n-pentyloxyphenyl, 4-n-hexyloxyphenyl, 4-n-heptyloxyphenyl, 4-n-octyloxyphenyl, 4-phenoxyphenyl, 4-biphenyl, 4-trichloromethoxyphenyl, 2,4-difluorophenyl, 2,6-difluorophenyl, 2,3-difluorophenyl, 3,5-difluorophenyl, 2,5-difluorophenyl, 3,4-difluorophenyl, 2,4-dichlorophenyl, 2,6-dichlorophenyl, 2,3-dichlorophenyl, 2,5-dichlorophenyl, 3,5-dichlorophenyl, 3,4-dichlorophenyl, 2,3-dimethylphenyl, 2,5-dimethylphenyl, 2,6-dimethylphenyl, 3,4-dimethylphenyl, 2,5-dimethoxyphenyl, 2,6-dimethoxyphenyl, 2,4-dimethoxyphenyl, 3,4-dimethoxyphenyl, 3,5-dimethoxyphenyl, 3,5-bis(trifluoromethyl)phenyl, 3,4-methylenedioxyphenyl, 2,4,6-trimethylphenyl, 3,4,5-trimethoxyphenyl and 2,4,6-triisopropylphenyl. As the most preferred examples for $R^2$, when $R^2$ is bonded to nitrogen at the 1-position of the pyrazolopyridine ring, $R^2$ is methyl, ethyl, n-propyl, i-propyl, n-butyl, i-butyl, sec-butyl, t-butyl, 2,2,2-trifluoroethyl, 2-hydroxyethyl, cyclohexyl, benzyl, 2-chlorobenzyl, 2-hydroxybenzyl, 3-trifluoromethylbenzyl, 2-phenylethyl, phenyl, 2-, 3- or 4-chlorophenyl, 2-, 3 or 4-bromophenyl, 2-, 3 or 4-fluorophenyl, 2-, 3- or 4-tolyl, 2-, 3- or 4-trifluoromethylphenyl, 3- or 4-methoxyphenyl, 2-hydroxyphenyl, 4-isopropylphenyl, 4-t-butylphenyl, 4-trifluoromethoxyphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2,3,4-trichlorophenyl, 2,4-difluorophenyl, 3,5-bis(trifluoromethyl)phenyl, 3-chloro-4-tolyl, 3-chloro-6-tolyl, 4-chloro-2-tolyl, 2-chloro-6-tolyl, 2-chloro-6-fluorophenyl, 2-chloro-5-trifluoromethylphenyl, 3-chloro-4-fluorophenyl, 4-bromo- 3-chlorophenyl, 2-chloro-4-trifluoromethylphenyl, 3-fluoro-6-tolyl, α-naphthyl, 2-pyridyl, 3-methyl-5-trifluoromethyl-2-pyridyl, 4-pyridyl or 2,6-dichloro-4-pyridyl.

As the most preferred combinations of $R^3$ and $R^4$, there may be mentioned that $R^3$ is hydrogen and $R^4$ is 4-chloro or 4-fluoro.

The most preferred examples for $R^5$ include i-propyl and cyclopropyl.

The most preferred example for Y includes (E)--CH=CH--.

Now, particularly preferred specific compounds of the present invention will be presented. The following compounds (a) to (z) are shown in the form of carboxylic acids. However, the present invention includes not only the compounds in the form of carboxylic acids but also the corresponding lactones formed by the condensation of the carboxylic acids with hydroxy at the 5-position, and sodium salts and lower alkyl esters (such as methyl, ethyl, i-propyl and n propyl esters) of the carboxylic acids, which can be physiologically hydrolyzed to the carboxylic acids.

(a)  (E)-3,5-dihydroxy-7-[4'-(4''-fluorophenyl)-1',3'-dimethyl-6'-(1''-methylethyl)pyrazolo[3,4-b]pyridin-5'-yl]hept-6-enoic acid.

(b)  (E)-3,5-dihydroxy-7-[6'-cyclopropyl-4'(4''-fluorophenyl)-1',3'-dimethylpyrazolo[3,4-b]pyridin-5'-yl]hept-6-enoic acid.

(c) (E)-3,5-dihydroxy-7-[1'-t-butyl-4'-(4''-fluorophenyl)-3'-methyl-6'-(1''-methylethyl)pyrazolo[3,4-b]pyridin-5'-yl]hept-6-enoic acid.

(d)  (E)-3,5-dihydroxy-7-[1'-t-butyl-6'-cyclopropyl-4'-(4''-fluorophenyl)-3'-methylpyrazolo[3,4-b]pyridin-5'-yl]hept-6-enoic acid.

(e) (E)-3,5-dihydroxy-7-[1'-benzyl-4'-(4''-fluorophenyl)-3'-methyl-6'-(1''-methylethyl)pyrazolo[3,4-b]pyridin-5'-yl]hept-6-enoic acid.

(E)-3,5-dihydroxy-7-[1'-benzyl-6'-cyclopropyl-4'-(4''-fluorophenyl)-3'-methylpyrazolo[3,4-b]pyridin-5'-yl]hept-6-enoic acid.

(g)  (E)-3,5-dihydroxy-7-[4'-(4''-fluorophenyl)-1'-(4''-methoxyphenyl)-3'-methyl-6'-(1''-methylethyl)-pyrazolo[3,4-b]pyridin-5'-yl]hept-6-enoic acid.

(h)  (E)-3,5-dihydroxy-7-[6'-cyclopropyl-4'-(4''-fluorophenyl)-1'-(4''-methoxyphenyl)-3'-methylpyrazolo[3,4-b]pyridin-5'-yl]hept-6-enoic acid.

(i)  (E)-3,5-dihydroxy-7-[3'-cyclopropyl-4'-(4''-fluorophenyl)-1'-methyl-6'-(1''-methylethyl)pyrazolo[3,4-b]pyridin-5'-yl]hept-6-enoic acid.

(j)  (E)-3,5-dihydroxy-7-[3',6'-dicyclopropyl-4'-(4''-fluorophenyl)-1'-methylpyrazolo[3,4-b]pyridin-5'-yl]hept-6-enoic acid.

(k)  (E)-3,5-dihydroxy-7-[4'-(4''-fluorophenyl)-1'-methyl-6'-(1''-methylethyl)-3'-phenylpyrazolo[3,4-b]pyridin 5'-yl]hept-6-enoic acid.

(l)  (E)-3,5 dihydroxy-7-[6'-cyclopropyl-4'-(4''-fluorophenyl)-1'-methyl-3'-phenylpyrazolo[3,4-b]pyridin-5'-yl]hept-6-enoic acid.

(m)  (E)-3,5-dihydroxy-7-[3'-(4''-chlorophenyl) 4'-(4''-fluorophenyl)-1'-methyl-6'-(1''-methylethyl)-pyrazolo[3,4-b]pyridin-5'-yl]hept-6-enoic acid.

(n)  (E)-3,5-dihydroxy-7-[3'-(4''-chlorophenyl) 6'-cyclopropyl-4'-(4''-fluorophenyl)-1'-methylpyrazolo[3,4-b]pyridin-5'-yl]hept-6-enoic acid.

(o)  (E)-3,5-dihydroxy-7-[1'-ethyl-4'-(4''-fluorophenyl)-6'-(1''-methylethyl)-pyrazolo[3,4-b]pyridin-5'-yl]hept-6-enoic acid.

(E)-3,5-dihydroxy-7-[6'-cyclopropyl-1'-ethyl-4'-(4''-fluorophenyl)pyrazolo[3,4-b]pyridin-5'-yl]hept-6-enoic acid.

(q)  (E)-3,5-dihydroxy-7-[4'-(4''-fluorophenyl)-6'-(1''-methylethyl)-1'-phenylpyrazolo[3,4-b]pyridin-5'-yl]hept-6-enoic acid.

(r)  (E) 3,5-dihydroxy-7-[6'-cyclopropyl-4'-(4''-fluorophenyl)-1'-phenylpyrazolo[3,4-b]pyridin-5'-yl]hept-6-enoic acid.

(s) (E)-3,5-dihydroxy-7-[4'-(4''-fluorophenyl)-3'-methyl-6'-(1''-methylethyl)-1'-phenylpyrazolo[3,4-b]pyridin-5'-yl]hept-6-enoic acid.

(t)  (E)-3,5-dihydroxy-7-[6'-cyclopropyl-4'-(4''-fluorophenyl)-3'-methyl-1'-phenylpyrazolo[3,4-b]pyridin-5'-yl]hept-6-enoic acid.

(u)  (E)-3,5-dihydroxy-7-[3'-cyclopropyl-4'-(4''-fluorophenyl)-6'-(1''-methylethyl)-1'-phenylpyrazolo[3,4-b]pyridin-5'-yl]hept-6-enoic acid.

(v)  (E)-3,5-dihydroxy-7-[3',6'-dicyclopropyl-4'-(4''-fluorophenyl)-1'-phenylpyrazolo[3,4-b]pyridin-5'-yl]hept-6-enoic acid.

(w)  (E)-3,5-dihydroxy-7-[1'-t-butyl-3'-cyclopropyl-4'-(4''-fluorophenyl)-6'-(1''-methylethyl)pyrazolo[3,4-b]pyridin-5'-yl]hept-6-enoic acid.

(x) (E)-3, 5-dihydroxy-7-[1'-t-butyl-3',6'-dicyclopropyl-4'-(4''-fluorophenyl)pyrazolo[3,4-b]pyridin-5'-yl]hept-6-enoic acid.

(y) (E)-3,5-dihydroxy 7-[1'-t-butyl-4'-(4''-fluorophenyl)-6'-(1''-methylethyl)-3'-phenylpyrazolo[3,4-b]pyridin-5'-yl]hept-6-enoic acid.

(z)  (E)-3,5-dihydroxy-7-[1'-t-butyl-6'-cyclopropyl-4'(4''-fluorophenyl)-3'-phenylpyrazolo[3,4-b]pyridin-5'-yl]hept-6-enoic acid.

The mevalonolactones of the formula I can be prepared by the following reaction scheme.

Further, the compound of the formula X can be prepared by a method disclosed in J. Prakt. Chem., 79, 1, (1909) or Japanese Unexamined Patent Publication No. 65089/1984, or it can be prepared from 3,3-dichloroacrylonitrile (J. Org. Chem., 34, 3410 (1969), ibid., 36, 3386 (1971)) as the starting material via cyanoketene acetal obtained by a method disclosed in J. Org. Chem., 35, 828 (1970) (Japanese Examined Patent Publication No. 2541/1973).

The compound of the formula VII can be prepared from the compound of the formula X (Chem. Pharm.

Bull., 35, 3235 (1987) and Japanese Unexamined Patent Publication No. 65089/1984).
The enal III can also be prepared by Process Steps K, L and M.
Further, the primary alcohol VI can also be prepared by Process Steps P, S and T.
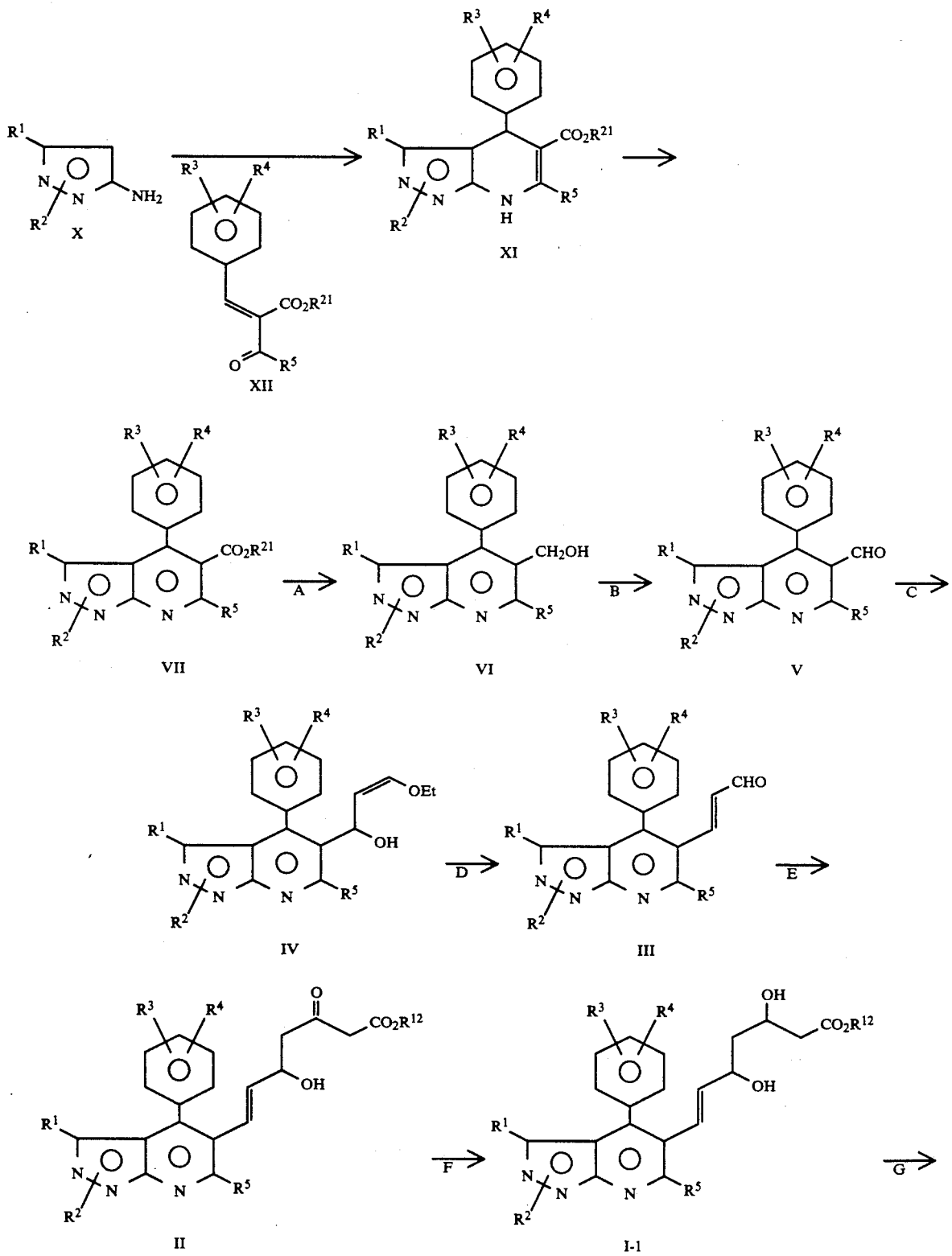

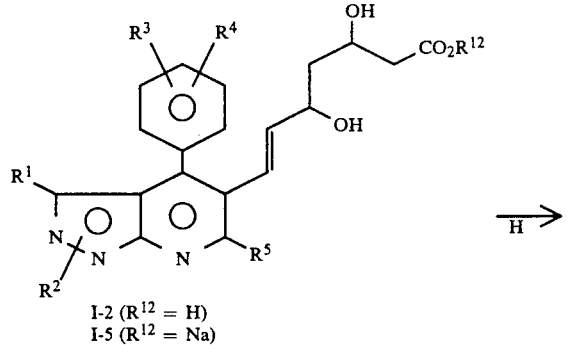
I-2 (R¹² = H)
I-5 (R¹² = Na)
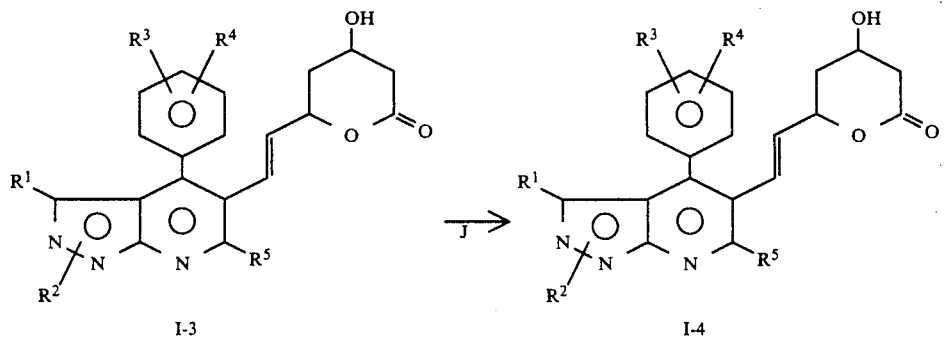
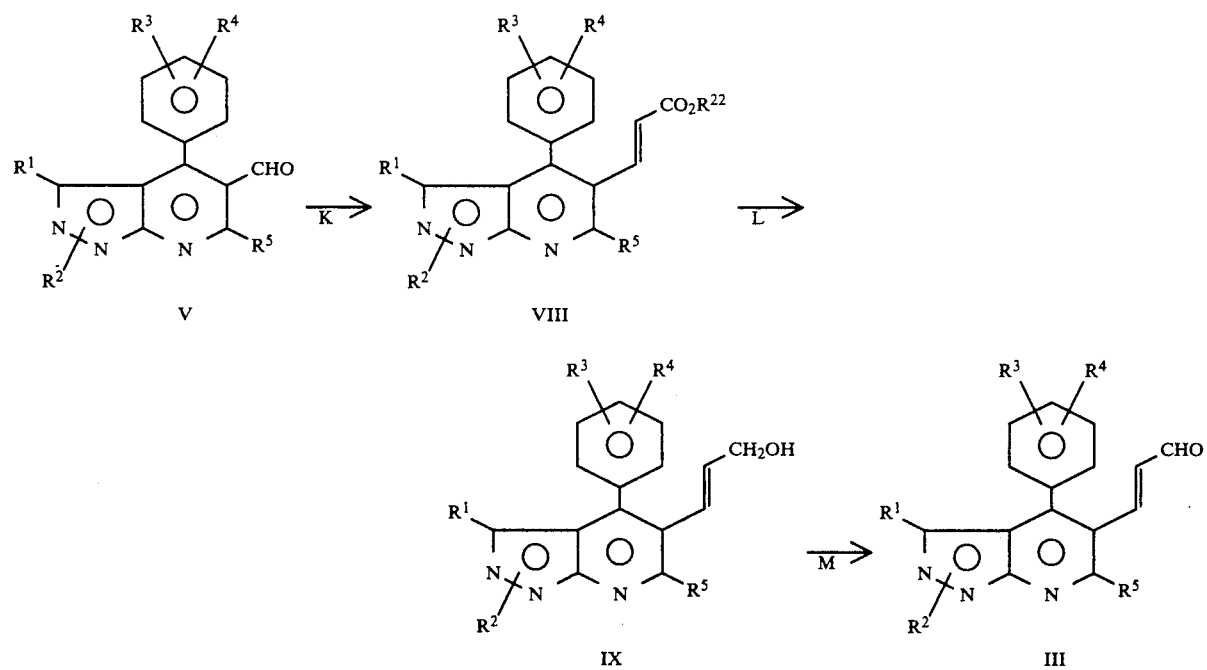
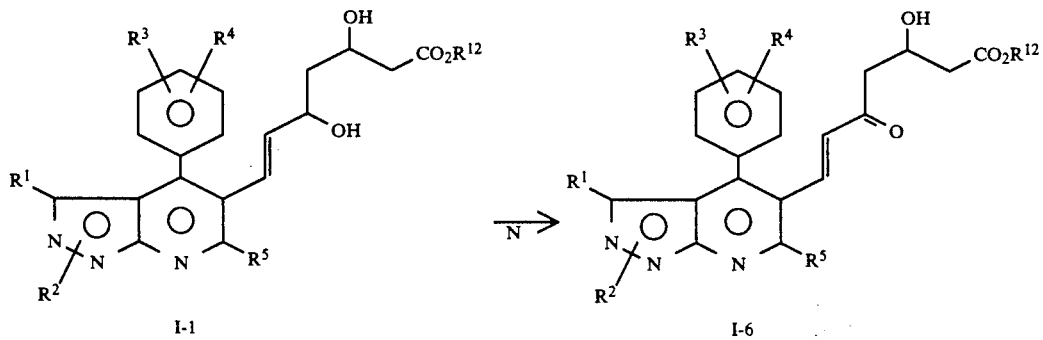

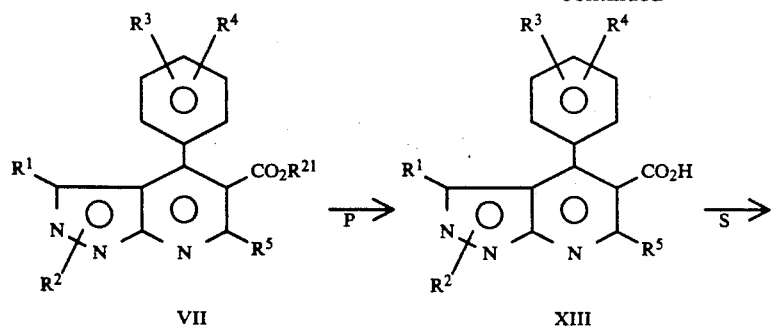
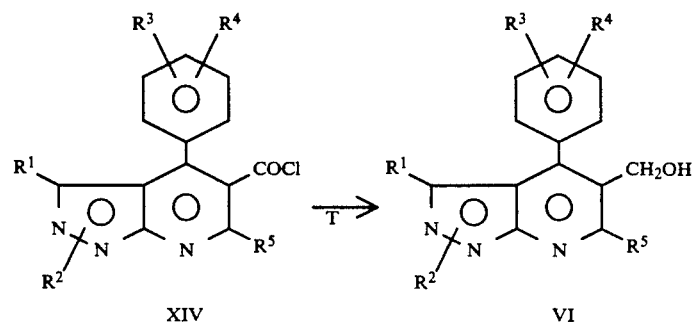
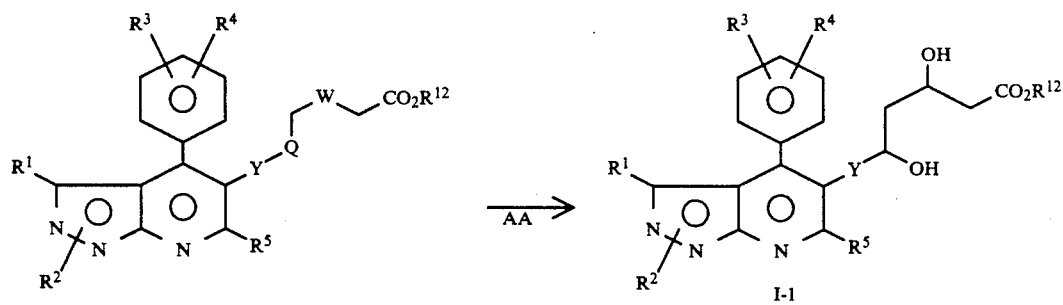
I-6 (Q = —C(O)—, W = —CH(OH)—, Y = —CH=CH—)
XV (Q = —CH(OH)—, W = —C(O)—, Y = —CH₂CH₂—)
I-1 (Y = —CH=CH—)
I-7 (Y = —CH₂CH₂—)
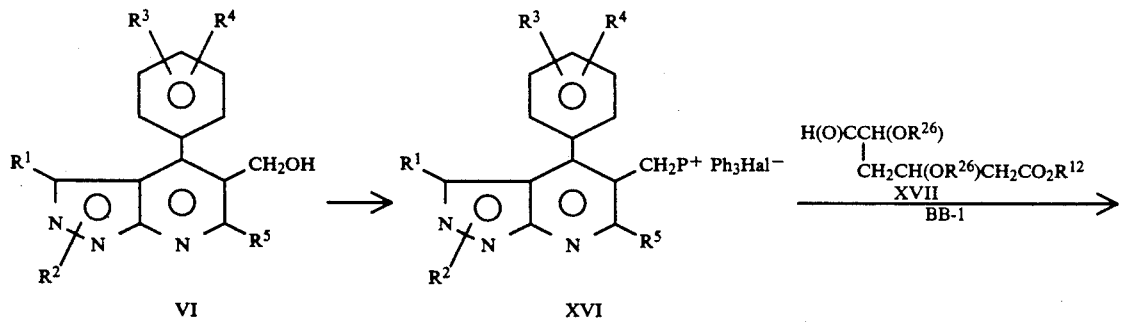
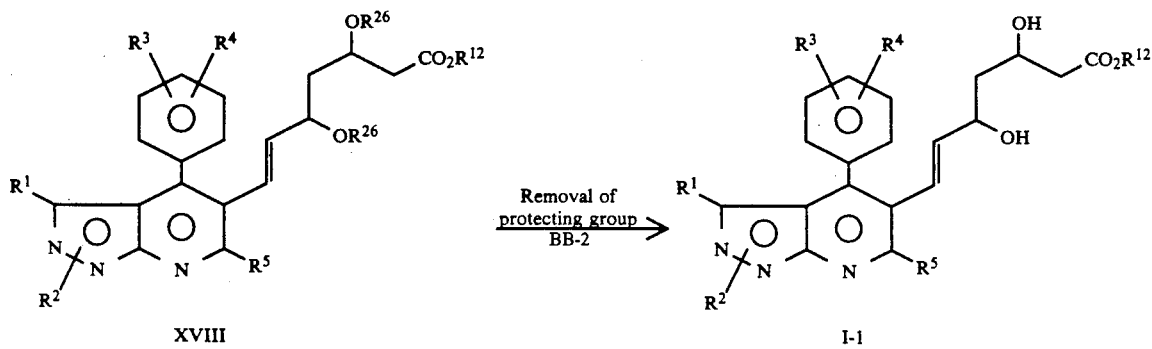

-continued

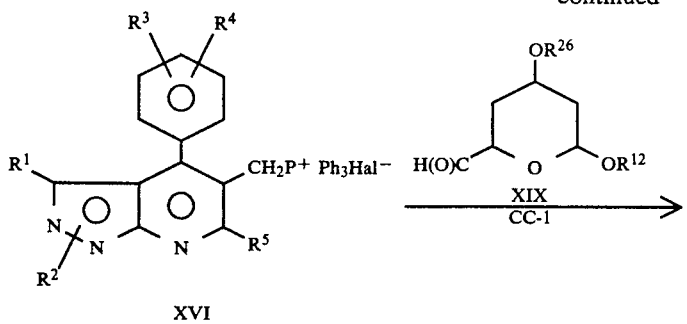

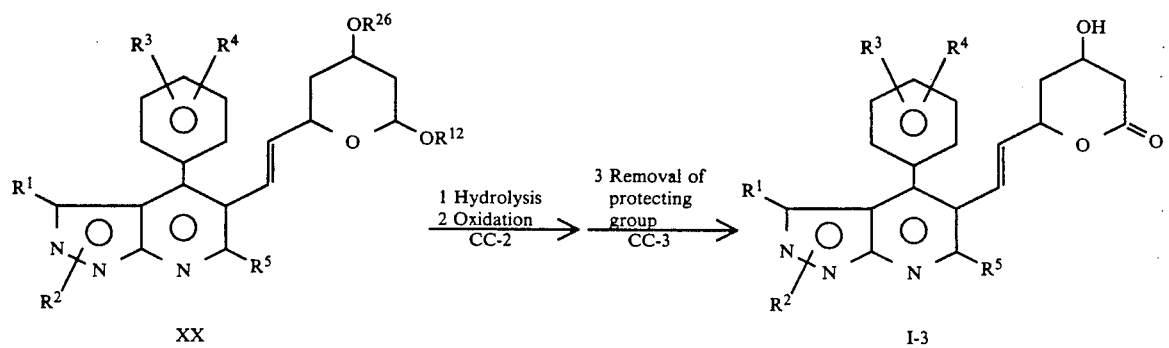

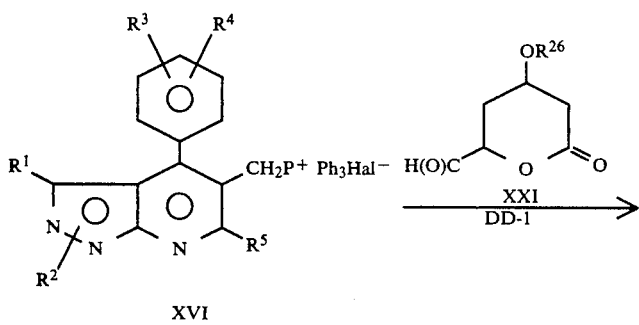

In the above reaction scheme, $R^1$, $R^2$, $R^3$, $R^4$, $R^5$ and $R^{12}$ are as defined above with respect to the formula I, and $R^{21}$ and $R^{22}$ independently represent $C_{1-4}$ lower alkyl such as methyl, ethyl, n propyl, i propyl or n-butyl.

Step A represents a reduction reaction of the ester to a primary alcohol. Such reduction reaction can be conducted by using various metal hydrides, preferably diisobutylaluminium hydride, in a solvent such as tetrahydrofuran, toluene or methylene chloride at a temperature of from $-20°$ to $20°$ C., preferably from $-10°$ to $10°$ C.

Step B represents an oxidation reaction of the primary alcohol to an aldehyde, which can be conducted by using various oxidizing agents. Preferably, the reaction can be conducted by using pyridinium chlorochromate in methylene chloride at a temperature of from $0°$ to $25°$ C., or by using oxalyl chloride, dimethyl sulfoxide and a tertiary amine such as triethylamine (Swern oxidation), or by using a sulfur trioxide pyridine complex.

Step C represents a synthesis of a 3-ethoxy-1-hydroxy-2-propene derivative, which can be prepared by reacting a compound V to a lithium compound which has been preliminarily formed by treating cis-1-ethoxy 2-(tri-n-butylstannyl)ethylene with butyl lithium in tetrahydrofuran.

As the reaction temperature, it is preferred to employ a low temperature at a level of from −60° to −78° C.

Step D represents a synthesis of an enal by acidic hydrolysis. As the acid catalyst, it is preferred to employ p-toluenesulfonic acid, hydrochloric acid or sulfuric acid, and the reaction may be conducted in a solvent mixture of water and tetrahydrofuran or ethanol at a temperature of from 10° to 25° C. The 3-ethoxy-1-hydroxy-2-propene derivative obtained in Step C can be used in Step D without purification i.e. by simply removing tetra-n-butyl tin formed simultaneously.

Step E represents a double anion addition reaction between the enal III and an acetoacetate. Such addition reaction is preferably conducted by using sodium hydride and n-butyl lithium as the base in tetrahydrofuran at a temperature of from −78° to 0° C., preferably from −30° to −10° C.

Step F represents a reduction reaction of the ketocarboxylate of the formula II, by various reducing agents. This reaction comprises reduction of carbonyl by e.g. sodium borohydride, sodium cyanoborohydride, zinc borohydride, disiamylborane, diborane, t-butylaminoborane, pyridine-borane complex, dicyclohexylborane, thexylborane, 9-borabicyclo[3.3.1]nonane, diisopinocamphenyl borane or lithium tri-sec-butyl borohydride to the corresponding dihydroxycarboxylate of the formula I-1.

This reaction can be conducted in a solvent selected from hydrocarbons, halogenated hydrocarbons, $C_{1-4}$ alcohols, ethers and solvent mixtures thereof, at a temperature of from −100° to 50° C., preferably from −78° to 30° C.

Further, as described in J. Amer. Chem. Soc., 105, 593 (1983), a trialkylborane such as tri n-butylborane or triethylborane and sodium borohydride are used at a low temperature. Further, as described in Tetrahedron Letters, 28, 155 (1987), the erythro form having biologically superior activities can advantageously be obtained by using an alkoxydialkylborane such as methoxydiethylborane or ethoxydiethylborane and sodium borohydride.

This reaction can be conducted by using a solvent mixture of $C_{1-4}$ alcohol and tetrahydrofuran at a temperature of from −80° to −50° C., preferably from −72° to −68° C.

Step G is a step for hydrolyzing the ester. The hydrolysis can be conducted by using an equimolar amount of a base, preferably potassium hydroxide or sodium hydroxide, in a solvent mixture of water and methanol or ethanol at a temperature of from 10° to 25° C. The free acid hereby obtained may be converted to a salt with a suitable base.

Step H is a step for forming a mevalonolactone by the dehydration reaction of the free hydroxy acid I 2. The dehydration reaction can be conducted in benzene or toluene under reflux while removing the resulting water or by adding a suitable dehydrating agent such as molecular sieve.

Further, the dehydration reaction may be conducted in dry methylene chloride by using a lactone-forming agent such as carbodiimide, preferably a water soluble carbodiimide such as N-cyclohexyl-N'-[2'-(methylmorpholinium)ethyl]carbodiimide p-toluene sulfonate at a temperature of from 10° to 35° C., preferably from 20° to 25° C.

Step J represents a reaction for hydrogenating the double bond connecting the mevalonolactone moiety and the pyrazolopyridine ring. This hydrogenation reaction can be conducted by using a catalytic amount of palladium-carbon or rhodium-carbon in a solvent such as methanol, ethanol, tetrahydrofuran or acetonitrile at a temperature of from 0° to 50° C., preferably from 10° to 25° C.

Step K represents a reaction for the synthesis of an $\alpha,\beta$-unsaturated carboxylic acid ester, whereby a transform $\alpha,\beta$-unsaturated carboxylic acid ester can be obtained by a so-called Horner-Wittig reaction by using an alkoxycarbonylmethyl phosphonate. The reaction is conducted by using sodium hydride or potassium t-butoxide as the base in dry tetrahydrofuran at a temperature of from −30° to 0° C., preferably from −20° to −15° C.

Step L represents a reduction reaction of the $\alpha, \beta$-unsaturated carboxylic acid ester to an allyl alcohol. This reduction reaction can be conducted by using various metal hydrides, preferably diisobutylaluminum hydride, in a solvent such as dry tetrahydrofuran or toluene at a temperature of from −10° to 10° C., preferably from −10° to 0° C.

Step M represents an oxidation reaction of the allyl alcohol to an enal. This oxidation reaction can be conducted by using various oxidizing agents, particularly activated manganese dioxide, in a solvent such as tetrahydrofuran, acetone, ethyl ether or ethyl acetate at a temperature of from 0° to 100° C., preferably from 15° to 50° C., or in accordance with Swern oxidation by using oxalyl chloride, dimethylsulfoxide and a tertiary amine such as triethylamine.

Step N represents a reaction for the synthesis of an $\alpha,\beta$-unsaturated ketone by the selective oxidation of the dihydroxy carboxylic acid ester. This reaction can be conducted by using activated manganese dioxide in a solvent such as ethyl ether, tetrahydrofuran, benzene or toluene at a temperature of from 20° to 80° C., preferably from 40° to 80° C.

Step P represents a hydrolysis reaction of an ester. The hydrolysis can be conducted under various acidic or basic conditions. It is preferred to employ a method wherein the heating or the refluxing are conducted by using sodium hydroxide or potassium hydroxide in a solvent mixture of water and ethyl alcohol or ethylene glycol, a method wherein the refluxing is conducted by using sodium ethoxide in ethyl alcohol, or a method wherein the hydrolysis is conducted by using trifluoroacetic acid at a temperature of from 0° to 70° C.

Step S represents a reaction for the synthesis of an acid chloride from the free carboxylic acid. The reaction can be conducted by using thionyl chloride or oxalyl chloride in a solvent such as benzene, tetrahydrofuran or methylene chloride at a temperature of from 0° to 80° C. The acid chloride XIV thereby obtained can be used in the following step without purification i.e. by simply removing the solvent.

Step T represents a reduction reaction of the acid chloride to a primary alcohol. Such reduction reaction can be conducted by using various metal hydride within a temperature range which does not affect other substituents.

For example, the reduction reaction can be conducted by using lithium aluminium hydride in an ether solvent such as diethyl ether at a temperature of from 0° to about 36° C., by using sodium borohydride in an ether solvent such as dioxane at a temperature of from 0° to about 100° C., by using sodium bis(2-methoxyethoxy)aluminium hydride in an aromatic hydrocarbon solvent such as benzene, toluene or xylene at a temperature of from 0° to the boiling point of the solvent, preferably from 25° to 80° C., or by using diisobutyl aluminium hydride in a solvent such as tetrahydrofuran, toluene or methylene chloride at a temperature of from −20° to 20° C., preferably from −10° to 10° C.

Further, the compound of the formula I-6 can be prepared from the aldehyde of the formula V by Wadsworth-Emmons coupling reaction (J. Amer. Chem. Soc., 107, 3731 (1985)). It can also be prepared from the enal of the formula III (Tetrahedron Letters, 26, 2951 (1985)).

Step AA represents a reduction reaction of the ketocarboxylate of the formula I-6 or XV by various reducing agents. This reaction comprises reduction of carbonyl by e.g. sodium borohydride, sodium cyanoborohydride, zinc borohydride, disiamylborane, diborane, t-butylaminoborane, pyridine-borane complex, dicyclohexylborane, thexylborane, 9-borabicyclo[3.3.1]nonane, diisopinocamphenyl borane or lithium tri-sec-butyl borohydride to the corresponding dihydroxycarboxylate of the formula I-1 or I-7.

This reaction can be conducted in a solvent selected from hydrocarbons, halogenated hydrocarbons, $C_{1-4}$ alcohols, ethers and solvent mixtures thereof, at a temperature of from −100° to 50° C., preferably from −78° to 30° C.

Further, as described in J. Amer. Chem. Soc., 105, 593 (1983), a trialkylborane such as tri n-butylborane or triethylborane and sodium borohydride are used at a low temperature. Further, as described in Tetrahedron Letters, 28, 155 (1987), the erythro form having biologically superior activities can advantageously be obtained by using an alkoxydialkylborane such as methoxydiethylborane or ethoxydiethylborane and sodium borohydride.

This reaction can be conducted by using a solvent mixture of $C_{1-4}$ alcohol and tetrahydrofuran at a temperature of from −80° to −50° C., preferably from −72° to −68° C.

The compound of the formula XV can be prepared by continuous Wittig reaction of the aldehyde of the formula V (WO-84/02131), followed by the double anion condensation reaction of the resulting aldehyde with an acetoacetate in the same manner as in Step E.

The substituents $R^1$, $R^2$, $R^3$, $R^4$ and $R^5$ of the intermediate material of the formula VI used in the reaction of Step BB-1, CC-1 or DD-1, and of the compound XVIII, XX or XXII are substituents defined with respect to the formula I excluding substituents having hydroxyl, amino or monoalkylamino.

Steps BB-1 and BB-2 comprise reacting the compound of the formula XVII with the compound of the formula XVI (wherein Hal is chlorine, bromine or iodine) by Wittig reaction to obtain the compound of the formula XVIII, (Step BB-1), followed by hydrolysis of the hydroxyl-protecting group ($R^{26}$) of the compound XVIII in the presence of a catalyst to obtain the compound of the formula I-1.

The phosphonium compound of the formula XVI can be obtained by halogenating the hydroxyl group of the hydroxymethyl at the 5-position of the pyrazolopyridine ring of the compound of the formula VI by a usual method, and then, reacting triphenylphosphine therewith.

The reactions of Steps BB-1 and BB-2 can be conducted in accordance with the method disclosed in Tetrahedron Letters, 25, 2435 (1984), U.S. Pat. No. 4,650,890, EP 0 244 364A, etc.

Wittig reaction can be conducted in a dry inert solvent. As the inert solvent, an aliphatic hydrocarbon, toluene or an ether type solvent may be mentioned. Preferred is the ether type solvent, such as diethyl ether, 1,2-diethoxyethane, 1,2-dimethoxyethane or tetrahydrofuran.

Wittig reaction can be conducted in a usual manner. A strong base is added to a solution of the phosphonium compound of the formula XVI within a temperature range which does not affect the substituents of the phosonium compound, to form the corresponding ylide compound, and then, the aldehyde of the formula XVII is added to the solution to form the desired compound.

As examples of the strong base, sodium hydride and n-butyl lithium may be mentioned, and preferred is n-butyl lithium.

The temperature upon the addition of the strong base is from −40° to 25° C., and the temperature upon the addition of the aldehyde is −35° to 30° C.

The hydroxyl-protecting group ($R^{26}$) of the compound of the formula XVII or XVIII is tri-substituted silyl, preferably diphenyl-t-butylsilyl, which is usually used as a hydroxyl-protecting group. Preferred is a protecting group which can be removed without decomposition of the ester or the lactone. The solvent used for the removal of the protecting group is an inert solvent such as tetrahydrofuran or methanol. The catalyst used for the removal of the protecting group is one commonly used for the reaction for removal of silyl. For example, a mixture of acetic acid and tetrabutylammonium fluoride in tetrahydrofuran, or hydrochloride in methanol, may be mentioned.

The reaction temperature for the removal of the protecting group is from 20° to 60° C., preferably from 20° to 30° C.

When there are hydroxyl-protecting groups other than $R^{26}$ at the time of the removal of the protecting group, such protecting groups may be removed to form hydroxyls.

Steps CC-1 to CC-3 represent Wittig reaction of the compound of the formula XVI with the compound of the formula XIX (Step CC-1), followed by hydrolysis of the acetal to form the hemiacetal, by oxidation of the hemiacetal to form the lactone (Step CC-2), and then, by removal of the hydroxyl-protecting group ($R^{26}$) (Step CC-3).

The hydroxyl-protecting group ($R^{26}$) is as defined in Steps BB-1 and BB-2.

The reaction condition for Step CC-1 may be the same as in the method of Step BB 1.

Step CC-2 represents (1) the hydrolysis and (2) the oxidation. The hydrolysis can be conducted in a solvent mixture such as 10% HCl in tetrahydrofuran or acetic acid/water/tetrahydrofuran, preferably acetic acid/water/tetrahydroruran.

The reaction temperature is from 10° to 100° C., preferably from 20° to 60° C.

The oxidation of the hemiacetal formed by the hydrolysis can be conducted under a mild condition. The reaction condition varies depending upon the type of the oxidizing agent used.

When the oxidizing agent is pyridinium chlorochromate, the reaction temperature is from 20° to 30° C., and the solvent used is halogenated hydrocarbons, preferably methylene chloride.

Swern oxidation is conducted by using a mixture system of oxalyl chloride/dimethylsulfoxide/triethylamine as the oxidizing agent, the reaction temperature is −60° to −40° C., and the solvent used is a halogenated hydrocarbon, preferably methylene chloride.

When the oxidizing agent is N-methylmorpholinoxide and dichloro-tris((phenyl)$_3$P)-ruthenium II, the reaction temperature is from 0° to 40° C., preferably from 20° to 30° C., and the solvent is dry dimethylformamide or acetone.

When the oxidizing agent is AgCO$_3$ on Celite, the reaction temperature is from 0° C. to the boiling point of the reaction solution, preferably at most 150° C., and the solvent is benzene, toluene, xylene, etc.

The reaction condition for the removal of the protecting group in Step CC-3 may be the same as in the method of Step BB-2.

Steps DD 1 and DD-2 represent Wittig reaction of the compound of the formula XVI with the compound of the formula XXI (Step DD-1) followed by removal of the hydroxyl-protecting group (R$^{26}$) (Step DD-2).

The hydroxyl-protecting group (R$^{26}$) is as defined in Steps BB-1 and BB-2.

The reaction condition for the Step DD-1 may be the same as in the method of Step BB-1.

The reaction condition for removing the protecting group in Step DD-2 may be the same as in the method of Step BB 2.

In Table 1, and in the following description, i-means iso, sec- means secondary, t- means tertiary and c-means cyclo. Likewise, Me means methyl, Et means ethyl, Pr means propyl, Bu means butyl, Pent means pentyl, Hex means hexyl and Ph means phenyl.

As specific examples of the compound of the present invention, the compounds of the formula I-2 are shown in Table 1 together with the compounds defined in Examples given hereinafter. In addition to the compound of the formula I-2 defined in Table 1, compounds of the formulas I-1, I-3 and I-4 wherein R$^1$, R$^2$, R$^3$, R$^4$ and R$^5$ are the same as those in the formula I-2, and compounds of the formula I-5 corresponding to the salts of the compound of the formula I-2, are also given in Table 1.

TABLE 1 (I-2)

| R$^1$ | R$^2$ | R$^3$ | R$^4$ | R$^5$ |
|---|---|---|---|---|
| H | 2-Ph | 4-F | H | i-Pr |
| H | 1-Me | 4-F | H | i-Pr |
| H | 2-Me | 4-F | H | i-Pr |
| H | 1-i-Pr | 4-F | H | i-Pr |
| H | 1-t-Bu | 4-F | H | i-Pr |
| H | 1-(4-Cl—Ph) | 4-F | H | i-Pr |
| H | 1-(4-Me—Ph) | 4-F | H | i-Pr |
| H | 1-(4-MeO—Ph) | 4-F | H | i-Pr |
| H | 1-(4-F—Ph) | 4-F | H | i-Pr |
| H | 1-CH$_2$Ph | 4-F | H | i-Pr |
| Me | 2-Me | 4-F | H | i-Pr |
| Me | 1-Et | 4-F | H | i-Pr |
| Me | 1-i-Pr | 4-F | H | i-Pr |
| Me | 1-(4-Cl—Ph) | 4-F | H | i-Pr |
| Me | 1-(4-Me—Ph) | 4-F | H | i-Pr |
| Me | 1-(4-F—Ph) | 4-F | H | i-Pr |
| Me | 1-(2'-pyridyl) | 4-F | H | i-Pr |

TABLE 1-continued (I-2)

| R$^1$ | R$^2$ | R$^3$ | R$^4$ | R$^5$ |
|---|---|---|---|---|
| Et | 1-Me | 4-F | H | i-Pr |
| Et | 1-Et | 4-F | H | i-Pr |
| Et | 1-i-Pr | 4-F | H | i-Pr |
| Et | 1-Ph | 4-F | H | i-Pr |
| cyclo-Pr | 1-Et | 4-F | H | i-Pr |
| cyclo-Pr | 1-i-Pr | 4-F | H | i-Pr |
| cyclo-Pr | 1-t-Bu | 4-F | H | i-Pr |
| i-Pr | 1-Me | 4-F | H | i-Pr |
| i-Pr | 2-Me | 4-F | H | i-Pr |
| i-Pr | 1-Et | 4-F | H | i-Pr |
| i-Pr | 1-i-Pr | 4-F | H | i-Pr |
| i-Pr | 1-t-Bu | 4-F | H | i-Pr |
| i-Pr | 2-Ph | 4-F | H | i-Pr |
| i-Pr | 1-Ph | 4-F | H | i-Pr |
| t-Bu | 1-Me | 4-F | H | i-Pr |
| t-Bu | 2-Me | 4-F | H | i-Pr |
| t-Bu | 1-Et | 4-F | H | i-Pr |
| t-Bu | 1-i-Pr | 4-F | H | i-Pr |
| t-Bu | 1-t-Bu | 4-F | H | i-Pr |
| t-Bu | 1-Ph | 4-F | H | i-Pr |
| Ph | 1-Et | 4-F | H | i-Pr |
| Ph | 1-i-Pr | 4-F | H | i-Pr |
| Ph | 1-t-Bu | 4-F | H | i-Pr |
| Ph | 1-Ph | 4-F | H | i-Pr |
| 4-Cl—Ph | 1-Et | 4-F | H | i-Pr |
| 4-Cl—Ph | 1-Ph | 4-F | H | i-Pr |
| 4-Me—Ph | 1-Me | 4-F | H | i-Pr |
| 4-MeO—Ph | 1-Me | 4-F | H | i-Pr |
| H | 1-Ph | 4-Cl | H | i-Pr |
| H | 1-Me | 4-Cl | H | i-Pr |
| H | 1-Et | 4-Cl | H | i-Pr |
| H | 1-i-Pr | 4-Cl | H | i-Pr |
| H | 1-t-Bu | 4-Cl | H | i-Pr |
| H | 1-Ph | 4-Cl | H | i-Pr |
| H | 1-(4-Cl—Ph) | 4-Cl | H | i-Pr |
| H | 1-(4-Me—Ph) | 4-Cl | H | i-Pr |
| H | 1-(4-MeO—Ph) | 4-Cl | H | i-Pr |
| H | 1-(4-F—Ph) | 4-Cl | H | i-Pr |
| H | 1-CH$_2$Ph | 4-Cl | H | i-Pr |
| Me | 1-Me | 4-Cl | H | i-Pr |
| Me | 1-Et | 4-Cl | H | i-Pr |
| Me | 1-i-Pr | 4-Cl | H | i-Pr |
| Me | 1-(4-Cl—Ph) | 4-Cl | H | i-Pr |
| Me | 1-(4-Me—Ph) | 4-Cl | H | i-Pr |
| Me | 1-(4-MeO—Ph) | 4-Cl | H | i-Pr |
| Me | 1-(4-F—Ph) | 4-Cl | H | i-Pr |
| Me | 1-t-Bu | 4-Cl | H | i-Pr |
| Me | 1-Ph | 4-Cl | H | i-Pr |
| Me | 1-CH$_2$Ph | 4-Cl | H | i-Pr |
| Me | 1-(2'-pyridyl) | 4-Cl | H | i-Pr |
| Et | 1-Me | 4-Cl | H | i-Pr |
| Et | 1-Et | 4-Cl | H | i-Pr |
| Et | 1-i-Pr | 4-Cl | H | i-Pr |
| Et | 1-Ph | 4-Cl | H | i-Pr |
| cyclo-Pr | 1-Me | 4-Cl | H | i-Pr |
| cyclo-Pr | 1-Et | 4-Cl | H | i-Pr |
| cyclo-Pr | 1-i-Pr | 4-Cl | H | i-Pr |
| cyclo-Pr | 1-t-Bu | 4-Cl | H | i-Pr |
| i-Pr | 1-Me | 4-Cl | H | i-Pr |
| i-Pr | 1-Et | 4-Cl | H | i-Pr |
| i-Pr | 1-i-Pr | 4-Cl | H | i-Pr |
| i-Pr | 1-t-Bu | 4-Cl | H | i-Pr |
| i-Pr | 1-Ph | 4-Cl | H | i-Pr |
| t-Bu | 1-Me | 4-Cl | H | i-Pr |
| t-Bu | 1-Et | 4-Cl | H | i-Pr |
| t-Bu | 1-i-Pr | 4-Cl | H | i-Pr |
| t-Bu | 1-t-Bu | 4-Cl | H | i-Pr |

TABLE 1-continued

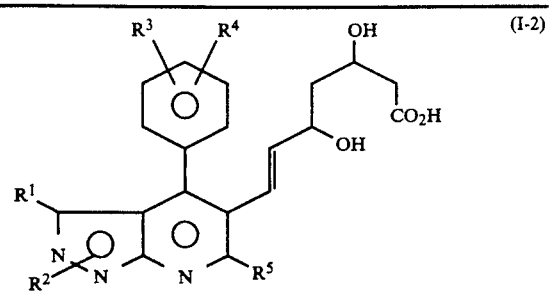

(I-2)

| R¹ | R² | R³ | R⁴ | R⁵ |
|---|---|---|---|---|
| t-Bu | 1-Ph | 4-Cl | H | i-Pr |
| Ph | 1-Et | 4-Cl | H | i-Pr |
| Ph | 1-i-Pr | 4-Cl | H | i-Pr |
| Ph | 1-t-Bu | 4-Cl | H | i-Pr |
| Ph | 1-Ph | 4-Cl | H | i-Pr |
| 4-Cl—Ph | 1-Me | 4-Cl | H | i-Pr |
| 4-Cl—Ph | 1-Et | 4-Cl | H | i-Pr |
| 4-Cl—Ph | 1-Ph | 4-Cl | H | i-Pr |
| 4-Me—Ph | 1-Me | 4-Cl | H | i-Pr |
| 4-MeO—Ph | 1-Me | 4-Cl | H | i-Pr |
| H | 1-Ph | H | H | i-Pr |
| H | 1-Me | H | H | i-Pr |
| H | 1-Et | H | H | i-Pr |
| H | 1-i-Pr | H | H | i-Pr |
| H | 1-t-Bu | H | H | i-Pr |
| H | 1-(4-Cl—Ph) | H | H | i-Pr |
| H | 1-(4-Me—Ph) | H | H | i-Pr |
| H | 1-(4-MeO—Ph) | H | H | i-Pr |
| H | 1-(4-F—Ph) | H | H | i-Pr |
| H | 1-CH₂Ph | H | H | i-Pr |
| Me | 1-Me | H | H | i-Pr |
| Me | 1-Et | H | H | i-Pr |
| Me | 1-i-Pr | H | H | i-Pr |
| Me | 1-(4-Cl—Ph) | H | H | i-Pr |
| Me | 1-(4-Me—Ph) | H | H | i-Pr |
| Me | 1-(4-MeO—Ph) | H | H | i-Pr |
| Me | 1-(4-F—Ph) | H | H | i-Pr |
| Me | 1-t-Bu | H | H | i-Pr |
| Me | 1-Ph | H | H | i-Pr |
| Me | 1-CH₂Ph | H | H | i-Pr |
| Me | 1-(2'-pyridyl) | H | H | i-Pr |
| Et | 1-Me | H | H | i-Pr |
| Et | 1-Et | H | H | i-Pr |
| Et | 1-i-Pr | H | H | i-Pr |
| Et | 1-Ph | H | H | i-Pr |
| cyclo-Pr | 1-Me | H | H | i-Pr |
| cyclo-Pr | 1-Et | H | H | i-Pr |
| cyclo-Pr | 1-i-Pr | H | H | i-Pr |
| cyclo-Pr | 1-t-Bu | H | H | i-Pr |
| i-Pr | 1-Me | H | H | i-Pr |
| i-Pr | 1-Et | H | H | i-Pr |
| i-Pr | 1-i-Pr | H | H | i-Pr |
| i-Pr | 1-t-Bu | H | H | i-Pr |
| i-Pr | 1-Ph | H | H | i-Pr |
| t-Bu | 1-Me | H | H | i-Pr |
| t-Bu | 1-Et | H | H | i-Pr |
| t-Bu | 1-i-Pr | H | H | i-Pr |
| t-Bu | 1-t-Bu | H | H | i-Pr |
| t-Bu | 1-Ph | H | H | i-Pr |
| Ph | 1-Et | H | H | i-Pr |
| Ph | 1-i-Pr | H | H | i-Pr |
| Ph | 1-t-Bu | H | H | i-Pr |
| Ph | 1-Ph | H | H | i-Pr |
| 4-Cl—Ph | 1-Me | H | H | i-Pr |
| 4-Cl—Ph | 1-Et | H | H | i-Pr |
| 4-Cl—Ph | 1-Ph | H | H | i-Pr |
| 4-Me—Ph | 1-Me | H | H | i-Pr |
| 4-MeO—Ph | 1-Me | H | H | i-Pr |
| H | 1-Ph | 4-F | H | c-Pr |
| H | 2-Ph | 4-F | H | c-Pr |
| H | 1-Me | 4-F | H | c-Pr |
| H | 2-Me | 4-F | H | c-Pr |
| H | 1-Et | 4-F | H | c-Pr |
| H | 1-i-Pr | 4-F | H | c-Pr |
| H | 1-t-Bu | 4-F | H | c-Pr |
| H | 1-(4-Cl—Ph) | 4-F | H | c-Pr |
| H | 1-(4-Me—Ph) | 4-F | H | c-Pr |
| H | 1-(4-MeO—Ph) | 4-F | H | c-Pr |
| H | 1-(4-F—Ph) | 4-F | H | c-Pr |
| H | 1-CH₂Ph | 4-F | H | c-Pr |
| Me | 2-Me | 4-F | H | c-Pr |
| Me | 1-Et | 4-F | H | c-Pr |
| Me | 1-i-Pr | 4-F | H | c-Pr |
| Me | 1-(4-Cl—Ph) | 4-F | H | c-Pr |
| Me | 1-(4-Me—Ph) | 4-F | H | c-Pr |
| Me | 1-(4-MeO—Ph) | 4-F | H | c-Pr |
| Me | 1-(4-F—Ph) | 4-F | H | c-Pr |
| Me | 1-Ph | 4-F | H | c-Pr |
| Me | 2-Ph | 4-F | H | c-Pr |
| Me | 1-CH₂Ph | 4-F | H | c-Pr |
| Me | 1-(2'-pyridyl) | 4-F | H | c-Pr |
| Et | 1-Me | 4-F | H | c-Pr |
| Et | 1-Et | 4-F | H | c-Pr |
| Et | 1-i-Pr | 4-F | H | c-Pr |
| Et | 1-Ph | 4-F | H | c-Pr |
| cyclo-Pr | 1-Me | 4-F | H | c-Pr |
| cyclo-Pr | 1-Et | 4-F | H | c-Pr |
| cyclo-Pr | 1-i-Pr | 4-F | H | c-Pr |
| cyclo-Pr | 1-Ph | 4-F | H | c-Pr |
| i-Pr | 1-Me | 4-F | H | c-Pr |
| i-Pr | 2-Me | 4-F | H | c-Pr |
| i-Pr | 1-Et | 4-F | H | c-Pr |
| i-Pr | 1-i-Pr | 4-F | H | c-Pr |
| i-Pr | 1-t-Bu | 4-F | H | c-Pr |
| i-Pr | 2-Ph | 4-F | H | c-Pr |
| i-Pr | 1-Ph | 4-F | H | c-Pr |
| t-Bu | 1-Me | 4-F | H | c-Pr |
| t-Bu | 2-Me | 4-F | H | c-Pr |
| t-Bu | 1-Et | 4-F | H | c-Pr |
| t-Bu | 1-i-Pr | 4-F | H | c-Pr |
| t-Bu | 1-t-Bu | 4-F | H | c-Pr |
| t-Bu | 1-Ph | 4-F | H | c-Pr |
| Ph | 1-Et | 4-F | H | c-Pr |
| Ph | 1-i-Pr | 4-F | H | c-Pr |
| Ph | 1-Ph | 4-F | H | c-Pr |
| 4-Cl—Ph | 1-Me | 4-F | H | c-Pr |
| 4-Cl—Ph | 1-Et | 4-F | H | c-Pr |
| 4-Cl—Ph | 1-Ph | 4-F | H | c-Pr |
| 4-Me—Ph | 1-Me | 4-F | H | c-Pr |
| 4-MeO—Ph | 1-Me | 4-F | H | c-Pr |
| H | 1-Ph | 4-Cl | H | c-Pr |
| H | 1-Me | 4-Cl | H | c-Pr |
| H | 1-Et | 4-Cl | H | c-Pr |
| H | 1-i-Pr | 4-Cl | H | c-Pr |
| H | 1-t-Bu | 4-Cl | H | c-Pr |
| H | 1-Ph | 4-Cl | H | c-Pr |
| H | 1-(4-Cl—Ph) | 4-Cl | H | c-Pr |
| H | 1-(4-Me—Ph) | 4-Cl | H | c-Pr |
| H | 1-(4-MeO—Ph) | 4-Cl | H | c-Pr |
| H | 1-(4-F—Ph) | 4-Cl | H | c-Pr |
| H | 1-CH₂Ph | 4-Cl | H | c-Pr |
| Me | 1-Me | 4-Cl | H | c-Pr |
| Me | 1-Et | 4-Cl | H | c-Pr |
| Me | 1-i-Pr | 4-Cl | H | c-Pr |
| Me | 1-(4-Cl—Ph) | 4-Cl | H | c-Pr |
| Me | 1-(4-Me—Ph) | 4-Cl | H | c-Pr |
| Me | 1-(4-MeO—Ph) | 4-Cl | H | c-Pr |
| Me | 1-(4-F—Ph) | 4-Cl | H | c-Pr |
| Me | 1-t-Bu | 4-Cl | H | c-Pr |
| Me | 1-Ph | 4-Cl | H | c-Pr |
| Me | 1-CH₂Ph | 4-Cl | H | c-Pr |
| Me | 1-(2'-pyridyl) | 4-Cl | H | c-Pr |
| Et | 1-Me | 4-Cl | H | c-Pr |
| Et | 1-Et | 4-Cl | H | c-Pr |

TABLE 1-continued

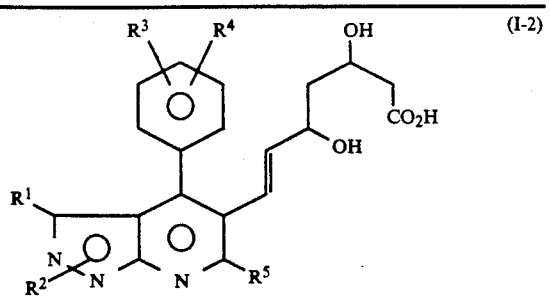
(I-2)

| R¹ | R² | R³ | R⁴ | R⁵ |
|---|---|---|---|---|
| Et | 1-i-Pr | 4-Cl | H | c-Pr |
| Et | 1-Ph | 4-Cl | H | c-Pr |
| cyclo-Pr | 1-Me | 4-Cl | H | c-Pr |
| cyclo-Pr | 1-Et | 4-Cl | H | c-Pr |
| cyclo-Pr | 1-i-Pr | 4-Cl | H | c-Pr |
| cyclo-Pr | 1-t-Bu | 4-Cl | H | c-Pr |
| i-Pr | 1-Me | 4-Cl | H | c-Pr |
| i-Pr | 1-Et | 4-Cl | H | c-Pr |
| i-Pr | 1-i-Pr | 4-Cl | H | c-Pr |
| i-Pr | 1-t-Bu | 4-Cl | H | c-Pr |
| i-Pr | 1-Ph | 4-Cl | H | c-Pr |
| t-Bu | 1-Me | 4-Cl | H | c-Pr |
| t-Bu | 1-Et | 4-Cl | H | c-Pr |
| t-Bu | 1-i-Pr | 4-Cl | H | c-Pr |
| t-Bu | 1-t-Bu | 4-Cl | H | c-Pr |
| t-Bu | 1-Ph | 4-Cl | H | c-Pr |
| Ph | 1-Et | 4-Cl | H | c-Pr |
| Ph | 1-i-Pr | 4-Cl | H | c-Pr |
| Ph | 1-t-Bu | 4-Cl | H | c-Pr |
| Ph | 1-Ph | 4-Cl | H | c-Pr |
| 4-Cl—Ph | 1-Me | 4-Cl | H | c-Pr |
| 4-Cl—Ph | 1-Et | 4-Cl | H | c-Pr |
| 4-Cl—Ph | 1-Ph | 4-Cl | H | c-Pr |
| 4-Me—Ph | 1-Me | 4-Cl | H | c-Pr |
| 4-MeO—Ph | 1-Me | 4-Cl | H | c-Pr |
| H | 1-Ph | H | H | c-Pr |
| H | 1-Me | H | H | c-Pr |
| H | 1-Et | H | H | c-Pr |
| H | 1-i-Pr | H | H | c-Pr |
| H | 1-t-Bu | H | H | c-Pr |
| H | 1-(4-Cl—Ph) | H | H | c-Pr |
| H | 1-(4-Me—Ph) | H | H | c-Pr |
| H | 1-(4-MeO—Ph) | H | H | c-Pr |
| H | 1-(4-F—Ph) | H | H | c-Pr |
| H | 1-CH₂Ph | H | H | c-Pr |
| Me | 1-Me | H | H | c-Pr |
| Me | 1-Et | H | H | c-Pr |
| Me | 1-i-Pr | H | H | c-Pr |
| Me | 1-(4-Cl—Ph) | H | H | c-Pr |
| Me | 1-(4-Me—Ph) | H | H | c-Pr |
| Me | 1-(4-MeO—Ph) | H | H | c-Pr |
| Me | 1-(4-F—Ph) | H | H | c-Pr |
| Me | 1-t-Bu | H | H | c-Pr |
| Me | 1-Ph | H | H | c-Pr |
| Me | 1-CH₂Ph | H | H | c-Pr |
| Me | 1-(2'-pyridyl) | H | H | c-Pr |
| Et | 1-Me | H | H | c-Pr |
| Et | 1-Et | H | H | c-Pr |
| Et | 1-i-Pr | H | H | c-Pr |
| Et | 1-Ph | H | H | c-Pr |
| cyclo-Pr | 1-Me | H | H | c-Pr |
| cyclo-Pr | 1-Et | H | H | c-Pr |
| cyclo-Pr | 1-i-Pr | H | H | c-Pr |
| cyclo-Pr | 1-t-Bu | H | H | c-Pr |
| i-Pr | 1-Me | H | H | c-Pr |
| i-Pr | 1-Et | H | H | c-Pr |
| i-Pr | 1-i-Pr | H | H | c-Pr |
| i-Pr | 1-t-Bu | H | H | c-Pr |
| i-Pr | 1-Ph | H | H | c-Pr |
| t-Bu | 1-Me | H | H | c-Pr |
| t-Bu | 1-Et | H | H | c-Pr |
| t-Bu | 1-i-Pr | H | H | c-Pr |
| t-Bu | 1-t-Bu | H | H | c-Pr |
| t-Bu | 1-Ph | H | H | c-Pr |
| Ph | 1-Et | H | H | c-Pr |
| Ph | 1-i-Pr | H | H | c-Pr |
| Ph | 1-t-Bu | H | H | c-Pr |

TABLE 1-continued

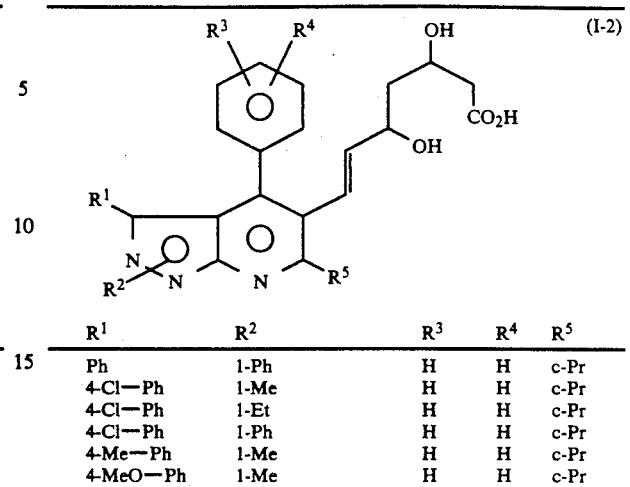
(I-2)

| R¹ | R² | R³ | R⁴ | R⁵ |
|---|---|---|---|---|
| Ph | 1-Ph | H | H | c-Pr |
| 4-Cl—Ph | 1-Me | H | H | c-Pr |
| 4-Cl—Ph | 1-Et | H | H | c-Pr |
| 4-Cl—Ph | 1-Ph | H | H | c-Pr |
| 4-Me—Ph | 1-Me | H | H | c-Pr |
| 4-MeO—Ph | 1-Me | H | H | c-Pr |

Further, pharmaceutically acceptable salts such as sodium salts or potassium salts or esters such as ethyl esters or methyl esters of these compounds can be prepared in the same manner.

The compounds of the present invention exhibit high inhibitory activities against the cholesterol biosynthesis wherein HMG-CoA reductase acts as a rate limiting enzyme, as shown by the test results given hereinafter, and thus are capable of suppressing or reducing the amount of cholesterol in blood as lipoprotein. Thus, the compounds of the present invention are useful as curing agents against hyperlipidemia, hyperlipoproteinemia and atheroscleosis.

They may be formulated into various suitable formulations depending upon the manner of the administration. The compounds of the present invention may be administered in the form of free acids or in the form of physiologically hydrolyzable and acceptable esters or lactones, or pharmaceutically acceptable salts.

The pharmaceutical composition of the present invention is preferably administered orally in the form of the compound of the present invention by itself or in the form of powders, granules, tablets or capsules formulated by mixing the compound of the present invention with a suitable pharmaceutically acceptable carrier including a binder such as hydroxypropyl cellulose, syrup, gum arabic, gelatin, sorbitol, tragacanth gum, polyvinyl pyrrolidone or CMC-Ca, an excipient such as lactose, sugar, corn starch, calcium phosphate, sorbitol, glycine or crystal cellulose powder, a lubricant such as magnesium stearate, talc, polyethylene glycol or silica, and a disintegrator such as potato starch.

However, the pharmaceutical composition of the present invention is not limited to such oral administration and it is applicable for parenteral administration. For example, it may be administered in the form of e.g. a suppository formulated by using oily base material such as cacao butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and an excipient such as lactose or corn starch, or a formulation for administration through mucous memberanes such as an ocular mucous membrane, a nasal mucous membrane and an oral mucous membrane.

Further, the compounds of the present invention may be combined with basic ion-exchange resins which are capable of binding bile acids and yet not being absorbed by the gastrointestinal tract.

The daily dose of the compound of the formula I is from 0.05 to 500 mg, preferably from 0.5 to 50 mg, for an adult. It is administered from once to three times per day. The dose may of course be varied depending upon the age, the weight or the condition of illness of the patient.

The compounds of the formulas II to VII are novel, and they are important intermediates for the preparation of the compounds of the formula I. Accordingly, the present invention relates also to the compounds of the formulas II to VII and the processes for their production.

Now, the present invention will be described in further detail with reference to Test Examples for the pharmacological activities of the compounds of the present invention, their Preparation Examples and formulation Examples. However, it should be understood that the present invention is by no menas restricted by such specific Examples.

PHARMACOLOGICAL TEST EXAMPLES

Test A: Inhibition of cholesterol biosynthesis from acetate in vitro

Enzyme solution was prepared from liver of male Wistar rat billialy connulated and discharged bile for over 24 hours. Liver was cut out at mid-dark and microsome and supernatant fraction which was precipitable with 40–80% of solution of ammonium sulfate (sup fraction) were prepared from liver homogenate according to the modified method of Knauss et. al.; Kuroda, M., et. al., Biochim. Biophys. Acta, 489, 119 (1977). For assay of cholesterol biosynthesis, microsome (0.1 mg protein) and sup fraction (1.0 mg protein) were incubated for 2 hours at 37° C. in 200 µl of the reaction mixture containing ATP; 1 mM, Glutathione; 6 mM, Glucose-1-phosphate; 10 mM, NAD; 0.25 mM, NADP; 0.25 mM, CoA; 0.04 mM and 0.2 mM [2-$^{14}$C]sodium acetate (0.2 µCi) with 4 µl of test compound solution dissolved in water or dimethyl sulfoxide. To stop reaction and saponify, 1 ml of 15% EtOH-KOH was added to the reactions and heated at 75° C. for 1 hour. Nonsaponifiable lipids were extracted with petroleum ether and incorporated $^{14}$C radioactivity was counted. Inhibitory activity of compounds was indicated with IC50.

Test B Inhibition of cholesterol biosynthesis in culture cells

Hep G2 cells at over 5th passage were seeded to 12 well plates and incubated with Dulbecco's modified Eagle (DME) medium containing 10% of fetal bovine serum (FBS) at 37° C., 5% CO$_2$ until cells were confluent for about 7 days. Cells were exposed to the DME medium containing 5% of lipoprotein deficient serum (LpDS) prepared by ultracentrifugation method for over 24 hours. Medium was changed to 0.5 ml of fresh 5% LpDS containing DME before assay and 10 µl of test compound solution dissolved in water or DMSO were added. 0.2 µCi of [2-$^{14}$C]sodium acetate (20 µl) was added at 0 hr(B-1) or 4 hrs(B-2) after addition of compounds. After 4 hrs further incubation with [2-$^{14}$C]sodium acetate, medium was removed and cells were washed with phosphate buffered saline (PBS) chilled at 4° C. Cells were scraped with rubber policeman and collected to tubes with PBS and digested with 0.2 ml of 0.5 N KOH at 37° C. Aliquot of digestion was used for protein analysis and remaining was saponified with 1 ml of 15% EtOH-KOH at 75° C. for 1 hour. Nonsaponifiable lipids were extracted with petroleum ether and $^{14}$C radioactivity was counted. Counts were revised by cell protein and indicated with DPM/mg protein. Inhibitory activity of compounds was indicated with IC50.

Test C: Inhibition of cholesterol biosynthesis in vivo

Male Sprague-Dawley rats weighing about 150 g were fed normal Purina chow diet and water ad libitum, and exposed to 12 hours light/12 hours dark lighting pattern (2:00 PM–2:00 AM dark) prior to use for in vivo inhibition test of cholesterol biosynthesis. Animals were separated groups consisting of five rats as to be average mean body weight in each groups. Test compounds at dosage of 0.02–0.2 mg/kg body weight (0.4 ml/100 g body weight), were dissolved in water or suspended in 0.5% methyl cellulose and orally administered at 2–3 hours before mid-dark (8:00 PM), while cholesterol biosynthesis reaches to maximum in rates. As control, rats were orally administered only water or vehicle. At 90 minutes after sample administration, rats were injected intraperitoneally with 10 µCi of [2-$^{14}$C]sodium acetate at volume of 0.2 ml per one. 2 Hours later, blood samples were obtained and serum were separated immediately. Total lipids were extracted according to the method of Folch et al. and saponified with EtOH-KOH. Nonsaponifiable lipids were extracted with petroleum ether and radio activity incorporated into nonsaponifiable lipids was counted.

Inhibitory activity was indicated as percent decrease of counts in testing groups (DPM/2 ml serum/2 hours) from that in control group.

With respect to the compounds of the present invention, the inhibitory activities against the cholesterol biosynthesis in which HMG-CoA reductase serves as a rate limiting enzyme, were measured by the above Test A and B. The results are shown in Tables 2, 2-2, 3, 3-2 and 3-3. Further, the results of the measurements by Test C are also presented.

TABLE 2

| Inhibitory activities of reference compound by Test A | |
|---|---|
| Reference compound | IC50 (molar concentration) |
| CS-514 | 1.1 × 10$^{-8}$ |

In Table 2-2, the relative activities are shown based on the activities of CS-514 by Test A being evaluated to be 1.

TABLE 2-2

| Relative activities by Test A | |
|---|---|
| Compound of the present invention | Relative activities |
| I-5-1 | 9.6 |
| I-5-2 | 3.1 |
| I-5-4 | 3.0 |
| I-5-5 | 11.8 |
| I-5-6 | 7.5 |
| I-5-9 | 5.8 |
| I-5-13 | 5.1 |
| I-5-14 | 7.9 |

Structures of reference compounds:

(1) CS-514

[Chemical structure of CS-514]

TABLE 3

| Inhibitory activities of Test B-1 | |
|---|---|
| Reference compound | IC50 (molar concentration) |
| CS-514 | $1.1 \times 10^{-6}$ |

In Table 3-2, the relative activities are shown based on the activities of CS-514 by Test B-1 being evaluated to be 1.

TABLE 3-2

| Relative activities by Test B-1 | |
|---|---|
| Compound of the present invention | Relative activities |
| I-1-5 | 204 |
| I-1-6 | 59 |
| I-1-9 | 103 |
| I-1-12 | 29 |
| I-5-13 | 149 |
| I-5-1 | 15 |
| I-5-2 | 0.8 |
| I-5-4 | 5.5 |
| I-5-7 | 31 |
| I-5-8 | 39 |
| I-5-10 | 17 |
| I-5-14 | 14.1 |
| I-5-15 | 10.6 |
| II-11 | 187 |

Further, the Test B-1, the inhibitory activities of the compound of the present invention at a concentration of $1.0 \times 10^{-7}$ mol/l are shown in Table 3-3.

TABLE 3-3

| Inhibitory activities of the compound of the present invention at a concentration of $1.0 \times 10^{-7}$ mol/l by Test B-1 | |
|---|---|
| Compound of the present invention | Relative activities |
| I-5-3 | 36.3 |
| I-5-5 | 78.2 |
| I-5-6 | 53.3 |
| I-5-9 | 55.3 |
| I-5-11 | 58.8 |
| I-5-12 | 47.3 |
| I-5-13 | 55.5 |
| I-5-16 | 49.0 |
| I-5 17 | 36.0 |

Results of the measurement of the inhibitory activities by Test C

The percent decreases of counts after the oral administration of 0.2 mg/kg of compound I-5-4, I-5-5 and I-5-7 were 53%, 49% and 52%, respectively, relative to measured value of the control group. The percent decrease of counts after the oral administration of 0.2 mg/kg of CS-514 was 39% under the same condition.

The compounds of the present invention exhibited activities superior to the reference compound CS-514 in Tests A, B and C.

Test D: Acute toxicity

A 0.5% CMC suspension of a test compound was orally administered to ICR male mice (group of three mice). The acute toxicity was determined based on the mortality after seven days. With compound I-5-1, I-5-2, I-5-4, I-5-7, I-5-10, I-5-11, I-5-12, I-5-14 and I-5-15 of the present invention, the mortality was 0% even when they were orally administered in an amount of 1,000 mg/kg, respectively.

EXAMPLE 1

Ethyl (E)-7-[4'-(4''-fluorophenyl)-1',3'-dimethyl-6'-(1''-methylethyl)pyrazolo[3,4-b]pyridin-5'-yl]-3,5-dihydroxyhept-6-enoate (Compound I-1-1)

This compound was prepared by the synthesis comprising the following reaction steps Example 1-a to Example 1-g.

EXAMPLE 1-a

Ethyl 4-(4'-fluorophenyl)-1,3-dimethyl-6-(1'-methylethyl)-pyrazolo[3,4-b]pyridin-5-ylcarboxylate (Compound VII 1)

Synthesis of dihydro compound 2.22 g (0.02 mol) of 5-amino-1,3-dimethylpyrazole and 5.3 g (0.02 mol) of ethyl 2-(4'-fluorobenzylidene)-4-methyl-3-oxo-pentanoate were mixed and heated at about 130° C. for one hour. Substances having a low boiling point were distilled off under reduced pressure by a rotary evaporator. Then, the reaction mixture was dissolved in chloroform, washed with a sodium carbonate aqueous solution and with water and dried over anhydrous magnesium sulfate. Chloroform was evaporated, and the residual oil was purified by silica gel column chromatography to obtain dihydropyrazolo[3,4-b]pyridine (XI 1).

PNMR (CDCl$_3$)δppm: 0.81(d,J=7Jz,3H), 1.0–1.3(m,6H), 1.97(s,3H), 2.64(m,1H), 3.44(d,J=3Hz,1H), 3.81(s,3H), 4.06(q,J=7Hz,2H), 4.48(d,J=3Hz,1H), 6.84(m,4H)

Oxidation method 7.54 g of the dihydro compound obtained in the above step was dissolved in 15 ml of glacial acetic acid, and 2.2 g of chromic anhydride was added thereto. The mixture was stirred at room temperature (15° to 20° C.). After confirming the disappearance of the starting materials by thin layer chromatography, 100 ml of water was added thereto. The mixture was extracted with chloroform. The chloroform layer was shaked together with a saturated sodium carbonate aqueous solution and with water and then dried over anhydrous magensium sulfate.

Chloroform was distilled off. The residual oil was purified by silica gel column chromatography (eluent: 1% methanol/chloroform) to obtain the desired compound as white crystals.

Melting point: 60°–64° C., yield: 52% (based on aminopyrazole)

Oxidation method-2

1 g of the dihydro compound obtained in the above step was dissolved in acetone containing a small amount of ethanol, and potassium permanganate (1.5 mol times) was added thereto. The mixture was stirred at room temperature for one day. After confirming the complete disappearance of the unreacted dihydro compound by thin layer chromatography, manganese dioxide was removed by filtration. The filtrate was concentrated, and the residual oil was treated in the same manner as in Oxidation method-1 to obtain the desired compound.

Yield: 60% (based on aminopyrazole)

EXAMPLE 1-b 4-(4'-fluorophenyl)-5-hydroxymethyl-1,3-dimethyl 6-(1'-methylethyl)pyrazolo[3,4-b]pyridine (Compound VI-1)

5.0 g (0.014 mol) of the compound VII-1 was dissolved in dry toluene under a nitrogen atmosphere and cooled to 0° C. in an ice bath. To this solution, 35 ml of a 16 weight % diisobutylaluminium hydride-toluene solution was dropwise added, and then, the mixture was stirred at 0° C. for 2 hours. After confirming the complete disappearance of the compound VII-1 by thin layer chromatography, a saturated ammonium chloride aqueous solution was added thereto at 0° C. to terminate the reaction. Diethyl ether was added to the reaction mixture, and the organic layer was separated. The gelled substance was dissolved by an addition of a sodium hydroxide aqueous solution and newly extracted with ethyl ether. The ethyl ether extracts were put together and dried over anhydrous magnesium sulfate. The extract was separated by filtration, and the solvent was distilled off to obtain 3.9 g of the slightly yellow desired compound.

Yield: 88%, Melting point: 174°-175° C.

EXAMPLE 1 c

[4-(4'-fluorophenyl)-1,3-dimethyl-6-(1'-methylethyl)-pyrazolo[3,4-b]pyridin-5-yl]carboxyaldehyde (Compound V-1)

4.2 g (19 mmol) of pyridinium chlorochromate, 0.69 g of anhydrous sodium acetate and 3.8 g (12 mmol) of Compound VI-1 were suspended in 50 ml of dry dichloromethane at room temperature. The raction solution was stirred for one hour, and then, 100 ml of diethyl ether was added thereto. The mixture was thoroughly stirred. The reaction mixture was subjected to suction filtration through Celite layer, and the extract was evaporated under reduced pressure to dryness. The residue was subjected to silica gel column chromatography (elutent: chloroform) to obtain 2.9 g (yield: 78%) of the desired compound as slightly yellow substance.

Melting point: 144°-146° C.

EXAMPLES 1-d and 1-e (E)-3-[4'-(4''-fluorophenyl)-1',3'-dimethyl-6'-(1''-methylethyl)pyrazolo[3,4-b]pyridin-5'-yl ]propenealdehyde (Compound III-1)

EXAMPLE I-d 14.5 g (40 mmol) of cis-1-ethoxy-2-(tri-n-butylstannyl)ethylene was dissolved in 50 ml of dry tetrahydrofuran, and the solution was cooled to −78° C. under a nitrogen atmosphere. 26 ml (40 mmol) of a 15 weight % n-butyl lithium-n-hexane solution was dropwise added to this solution. The mixture was stirred for 20 minutes, and then, a solution of 2.5 g (8 mmol) of Compound V-1 dissolved in 20 ml of dry tetrahydrofuran was dropwise added thereto. The reaction mixture was stirred at −78° C. for one hour, and then, 26 ml of a saturated ammonium chloride solution was added thereto to terminate the reaction. The organic layer was extracted with diethyl ether. The ether extract was washed with a saturated sodium chloride aqueous solution and dried over anhydrous magensium sulfate. The solvent was distilled off under reduced pressure, and the residue was subjected to liquid separation between n-hexane and acetonitrile. The acetonitrile layer was subjected to distillation under reduced pressure to obtain substantially pure Compound IV-1.

EXAMPLE 1-e

Compound IV-1 obtained in Example 1-d was dissolved in 70 ml of tetrahydrofuran, and 20 ml of water and 3 g of p-toluenesulfonic acid were added thereto. The mixture was stirred at room temperature for 2 hours. The reaction solution was carefully neutralized with a sodium hydroxide aqueous solution. Then, diethyl ether was added thereto, and the extraction was conducted a few times. The extract was washed with a saturated sodium chloride aqueous solution and dried over anhydrous magnesium sulfate. Then, the solvent was distilled off under reduced pressure. The residue was subjected to silica gel column chromatography (eluent: ethyl acetate/n-hexane=1/9 (v/v)) to obtain the desired compound as yellow substance.

Quantity: 2.2 g (yield: 79%)

Melting point: 133°-134° C.

EXAMPLE 1-f

Ethyl (E)-7-[4'-(4''-fluorophenyl)-1',3'-dimethyl-6'-(1'''-methylethyl)pyrazolo[3,4-b]pyridin 5'-yl]-5-hydroxy-3-oxohepto-6-enoate (Compound II-1)

1.25 g of 60% sodium hydride was washed with dry petroleum ether, dried under a nitrogen stream and then suspended in 200 ml of dry tetrahydrofuran. The suspension was cooled to −15° C. under a nitrogen atmosphere, and 3.9 ml (30 mmol) of ethyl acetoacetate was dropwise added thereto. The mixture was stirred for 15 minutes. Then, 20 ml (30 mmol) of a 15 weight % (n-butyl lithium n hexane solution was dropwise added thereto, and the mixture was stirred for 30 minutes. Further, a solution of 2.1 g (6.1 mmol) of Compound III-1 dissolved in dry tetrahydrofuran was added thereto, and the mixture was stirred for one hour. 10 ml of a saturated ammonium chloride aqueous solution was added to the reaction mixture at −15° C, and the mixture was extracted three times with diethyl ether. The ether solution was washed with a saturated sodium chloride aqueous solution, dried over anhydrous magnesium sulfate and then evaporated under reduced pressure to dryness. The residue was subjected to silica gel column chromatrography (eluent: ethyl acetate/chloroform=1/9 (v/v)) to obtain 2.5 g (yield: 89%) of the desired compound as white substance.

Melting point: 95°-98° C.

EXAMPLE 1-g

Reduction method 1

Ethyl (E)-7-4'-(4"-fluorophenyl)-1',3'-dimethyl-6'-(1"-methylethyl)-pyrazolo[3,4-b]pyridin-5'-yl]-3,5-dihydroxyhept-6-enoate (Compound I-1-1)

2.32 g (4.96 mmol) of Compound II-1 was dissolved in 20 ml ethanol under a nitrogen atmosphere, and the mixture was cooled to 0° C. Then, 740 mg (20 mmol) of sodium borohydride was added thereto, and the mixture was stirred for one hour. The mixture was carefully neutralized by an addition of a 10% hydrochloric acid aqueous solution and then extracted three times with diethyl ether. The diethyl ether solution was washed with a saturated sodium chloride aqueous solution, dried over anhydrous magnesium sulfate and then evaporated under reduced pressure to dryness. The residual oil was purified by silica gel column chromatography (eluent: ethanol/chloroform=3/97 (v/v)) to obtain the pure desired product as colorless viscous oily substance.

Quantity: 1.81 g (yield: 78%)

NMR ($\delta$ppm in $CDCl_3$) 1.28(t,J=8Hz,3H), 1.32(d,J=8Hz,6H), 1.4 1.8(m,1H), 1.92(s,3H), 2.2-2.6(m,3H), 2.9-3.8(m,2H), 3.42(Heptalet,J=8Hz,1H), 4.06(s,3H), 4.1-4.6(m,4H), 5.1-5.5(m,1H), 6.4-6.7(m,1H), 6.9-7.3(m,4H)

Reduction method 2

Ethyl (E)-7-[6'-cyclopropyl-4'-(4"-fluorophenyl)-1'-methyl-3'-phenylpyrazolo[3,4-b]pyridin-5'-yl]-3,5-dihydroxyhept-6-enoate (Compound I 1-14)

200 ml of a diethyl ether solution of about 0.15 mol/l of zinc borohydride was stirred under a nitrogen atmosphere while cooling the solution at −70° C. A solution of 375 g (7.12×10$^{-3}$ mol) of Compound II-14 dissolved in 40 ml of dry diethyl ether was gradually added thereto along the wall of the reactor. Further, the reaction solution was stirred at −70° C. for 6 hours. After confirming the substantial disappearance of the starting material by thin layer chromatography, 40 ml of methanol and then 100 ml of water was added thereto at −70° C. to terminate the reaction. Diethyl ether and diluted acetic acid were added to the reaction solution to adjust pH to 4, and the product was extracted with diethyl ether.

The diethyl ether layer was washed with water until the diethyl ether layer became neutral, further washed with a saturated sodium chloride aqueous solution. The diethyl ether layer was dried over anhydrous magnesium sulfate, and then, the solvent was evaporated by an evaporator. The residue was subjected to silica gel column chromatography (eluent: benzene/ethyl acetate) to obtain 3.09 g (82.0%) of the desired compound as slightly yellow powder.

EXAMPLE 2

Sodium (E)-7[4'-4"-fluorophenyl)-1',3'-dimethyl-6'-(1"-methylethyl)pyrazolo[3,4-b]pyridin-5'-yl]-3,5-dihydroxyhept-6-enoate (Compound I-5-1)

200 mg (0.43 mmol) of Compound I-1-1 was dissolved in 2 ml of ethanol, and 0.85 ml of a 0.5 N sodium hydroxide aqueous solution was dropwise added thereto. The mixture was stirred at room temperature for one hour. Then, ethanol was distilled off under reduced pressure, 2 ml of water was added thereto and extracted with diethyl ether. The aqueous layer was freeze-dried to obtain 180 mg (yield: 91%) of hygroscopic slightly yellow powder.

Melting point: 258°–264° C. (decomposed)

In the same manner as in Example 1 a, Compounds VII-2 to VII-18 were prepared. Physical properties of the compounds thereby obtained were shown in the following Table.

TABLE 4

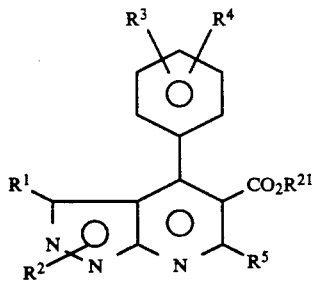

| Compound | $R^1$ | $R^2$ | $R^3$ | $R^4$ | $R^5$ | $R^{21}$ | Melting point (°C.) |
| --- | --- | --- | --- | --- | --- | --- | --- |
| VII-2 | Me | 1-Ph | 4-F | H | i-Pr | Et | 84–89 |
| VII-3 | Me | 2-Ph | 4-F | H | i-Pr | Et | 90–94 |
| VII-4 | Ph | 1-Me | 4-F | H | i-Pr | Et | Oil |
| VII-5 | Me | 1-Me | 4-F | H | c-Pr | Me | 121–123 |
| VII-6 | H | 1-Ph | 4-F | H | i-Pr | Et | 96–98 |
| VII-7 | Me | 1-t-Bu | 4-F | H | i-Pr | Et | 88–91 |
| VII-8 | H | 1-Et | 4-F | H | i-Pr | Et | Oil |
| VII-9 | c-Pr | 1-Me | 4-F | H | i-Pr | Et | 105–107 |
| VII-10 | Me | 1-Ph—$CH_2$ | 4-F | H | i-Pr | Et | 84–86 |
| VII-11 | 4-Cl—Ph | 1-Me | 4-F | H | i-Pr | Et | 138–141 |
| VII-12 | c-Pr | 1-Ph | 4-F | H | i-Pr | Et | 156–158 |
| VII-13 | Me | 1-(4-MeO—Ph) | 4-F | H | i-Pr | Et | 116–118 |
| VII-14 | Ph | 1-Me | 4-F | H | c-Pr | Me | 141–143 |
| VII-15 | Me | 1-t-Bu | 4-F | H | c-Pr | Me | 147–148 |
| VII-16 | c-Pr | 1-t-Bu | 4-F | H | c-Pr | Me | 115–120 |
| VII-17 | Ph | 1-t-Bu | 4-F | H | c-Pr | Me | 182–185 |

TABLE 4-continued

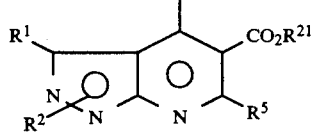

| Compound | R¹ | R² | R³ | R⁴ | R⁵ | R²¹ | Melting point (°C.) |
|---|---|---|---|---|---|---|---|
| VII-18 | Me | 1-(2-pyridyl) | 4-F | H | c-Pr | Me | 120–125 |

PNMR of Compound VII-4 (CDCl₃) δppm: 0.96(t,J=8Hz,3H), 1.42(d,J=7Hz,6H), 3.27(Heptalet,J=7Hz,1H), 4.02(q,J=8H,2H), 4.18(s,3H), 6.6–7.3(m,9H)

PNMR of Compound VII-8 (CDCl₃) δppm: 1.07(t,J=8Hz,3H), 1.42(d,J=7Hz,6H), 1.59(t,J=8Hz,3H), 3.41(Heptalet,J=7Hz,1H), 4.20(q,J=8Hz,2H), 4.70(q,J=8Hz,2H), 7.1–8.0(m,5H)

In the same manner as in Example 1-b, Compounds VI 2 to VI-17 were prepared. Physical properties of the compounds thereby obtained are shown in the following Table.

TABLE 5

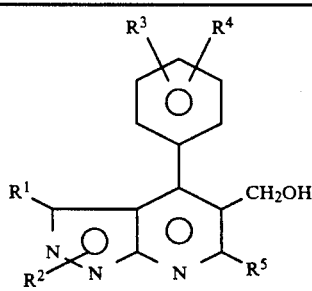

| Compound | R¹ | R² | R³ | R⁴ | R⁵ | Melting point (°C.) |
|---|---|---|---|---|---|---|
| VI-2 | Me | 1-Ph | 4-F | H | i-Pr | 139–141 |
| VI-3 | Me | 2-Ph | 4-F | H | i-Pr | 142–144 |
| VI-4 | Ph | 1-Me | 4-F | H | i-Pr | 237–239 |
| VI-5 | Me | 1-Me | 4-F | H | c-Pr | 168–170 |
| VI-6 | H | 1-Ph | 4-F | H | i-Pr | 189–192 |
| VI-7 | Me | 1-t-Bu | 4-F | H | i-Pr | 150–152 |
| VI-8 | H | 1-Et | 4-F | H | i-Pr | 149–148 |
| VI-9 | c-Pr | 1-Me | 4-F | H | i-Pr | 224–226 |
| VI-10 | Me | 1-Ph—CH₂ | 4-F | H | i-Pr | 162–164 |
| VI-11 | 4-Cl—Ph | 1-Me | 4-F | H | i-Pr | 216–218 |
| VI-12 | c-Pr | 1-Ph | 4-F | H | i-Pr | 196–198 |
| VI-13 | Me | 1-(4-MeO—Ph) | 4-F | H | i-Pr | 155–157 |
| VI-14 | Ph | 1-Me | 4-F | H | c-Pr | 214–215 |
| VI-15 | Me | 1-t-Bu | 4-F | H | c-Pr | 135–139 |
| VI-16 | c-Pr | 1-t-Bu | 4-F | H | c-Pr | 105–115 |
| VI-17 | Ph | 1-t-Bu | 4-F | H | c-Pr | 204–208 |

In the same manner as in Example 1-c, Compounds V-2 to V-18 were prepared. Physical properties of the compounds thereby obtained are shown in the following Table.

TABLE 6

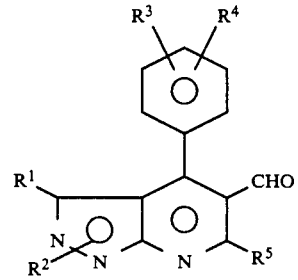

| Compound | R¹ | R² | R³ | R⁴ | R⁵ | Melting point (°C.) |
|---|---|---|---|---|---|---|
| V-2 | Me | 1-Ph | 4-F | H | i-Pr | 110–111 |
| V-3 | Me | 2-Ph | 4-F | H | i-Pr | 118–120 |
| V-4 | Ph | 1-Me | 4-F | H | i-Pr | 163–164 |
| V-5 | Me | 1-Me | 4-F | H | c-Pr | 149–151 |
| V-6 | H | 1-Ph | 4-F | H | i-Pr | 139–142 |
| V-7 | Me | 1-t-Bu | 4-F | H | i-Pr | 104–106 |
| V-8 | H | 1-Et | 4-F | H | i-Pr | 77–80 |
| V-9 | c-Pr | 1-Me | 4-F | H | i-Pr | 99–101 |
| V-10 | Me | 1-Ph—CH₂ | 4-F | H | i-Pr | 110–112 |
| V-11 | 4-Cl—Ph | 1-Me | 4-F | H | i-Pr | 164–167 |
| V-12 | c-Pr | 1-Ph | 4-F | H | i-Pr | 150–152 |
| V-13 | Me | 1-(4-MeO—Ph) | 4-F | H | i-Pr | 130–132 |
| V-14 | Ph | 1-Me | 4-F | H | c-Pr | 168–171 |
| V-15 | Me | 1-t-Bu | 4-F | H | c-Pr | 94–96 |
| V-16 | c-Pr | 1-t-Bu | 4-F | H | c-Pr | 122–125 |
| V-17 | Ph | 1-t-Bu | 4-F | H | c-Pr | 170–172 |
| V-18 | Me | 1-(2-pyridyl) | 4-F | H | c-Pr | 180–200 |

In the same manner as in Examples I-d and I-e, Compounds III-2 to III-18 were prepared. Physical properties of the compounds thereby obtained are shown in the following Table.

TABLE 7

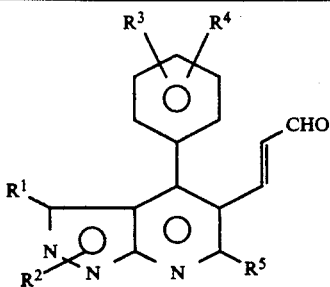

| Compound | R¹ | R² | R³ | R⁴ | R⁵ | Melting point (°C.) |
|---|---|---|---|---|---|---|
| III-2 | Me | 1-Ph | 4-F | H | i-Pr | 158–161 |
| III-3 | Me | 2-Ph | 4-F | H | i-Pr | 176–177.5 |
| III-4 | Ph | 1-Me | 4-F | H | i-Pr | 148–150 |
| III-5 | Me | 1-Me | 4-F | H | c-Pr | 135–137 |
| III-6 | H | 1-Ph | 4-F | H | i-Pr | 174–176 |
| III-7 | Me | 1-t-Bu | 4-F | H | i-Pr | 170–172 |
| III-8 | H | 1-Et | 4-F | H | i-Pr | 130–133 |
| III-9 | c-Pr | 1-Me | 4-F | H | i-Pr | 127–129 |
| III-10 | Me | 1-Ph—CH₂ | 4-F | H | i-Pr | 147–150 |
| III-11 | 4-Cl—Ph | 1-Me | 4-F | H | i-Pr | 88–90 |
| III-12 | c-Pr | 1-Ph | 4-F | H | i-Pr | 178–180 |
| III-13 | Me | 1-(4-MeO—Ph) | 4-F | H | i-Pr | 147–150 |
| III-14 | Ph | 1-Me | 4-F | H | c-Pr | <40 |
| III-15 | Me | 1-t-Bu | 4-F | H | c-Pr | 186–190 |
| III-16 | c-Pr | 1-t-Bu | 4-F | H | c-Pr | 192–195 |
| III-17 | Ph | 1-t-Bu | 4-F | H | c-Pr | 148–150 |
| III-18 | Me | 1-(2-pyridyl) | 4-F | H | c-Pr | 175–178 |

In the same manner as in Example 1-f, Compounds II-2 to II-18 were prepared. Physical properties of the compounds thereby obtained are shown in the following Table.

TABLE 8

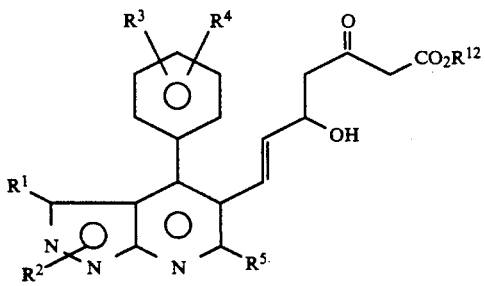

| Compound | R¹ | R² | R³ | R⁴ | R⁵ | R¹² | Melting point (°C.) |
|---|---|---|---|---|---|---|---|
| II-2 | Me | 1-Ph | 4-F | H | i-Pr | Et | 93–95 |
| II-3 | Me | 2-Ph | 4-F | H | i-Pr | Et | 87–94 |
| II-4 | Ph | 1-Me | 4-F | H | i-Pr | Et | Oil |
| II-5 | Me | 1-Me | 4-F | H | c-Pr | Et | Oil |
| II-6 | H | 1-Ph | 4-F | H | i-Pr | Et | 101–104 |
| II-7 | Me | 1-t-Bu | 4-F | H | i-Pr | Et | 66–69 |
| II-8 | H | 1-Et | 4-F | H | i-Pr | Et | 91–94 |
| II-9 | c-Pr | 1-Me | 4-F | H | i-Pr | Et | 68–72 |
| II-10 | Me | 1-Ph—CH₂ | 4-F | H | i-Pr | Et | Oil |
| II-11 | 4-Cl—Ph | 1-Me | 4-F | H | i-Pr | Et | 129–132 |
| II-12 | c-Pr | 1-Ph | 4-F | H | i-Pr | Et | 132–135 |
| II-13 | Me | 1-(4-MeO—Ph) | 4-F | H | i-Pr | Et | 131–133 |
| II-14 | Ph | 1-Me | 4-F | H | c-Pr | Et | Oil |
| II-15 | Me | 1-t-Bu | 4-F | H | c-Pr | Et | Oil |
| II-16 | c-Pr | 1-t-Bu | 4-F | H | c-Pr | Et | 103–107 |
| II-17 | Ph | 1-t-Bu | 4-F | H | c-Pr | Et | Oil |
| II-18 | Me | 1-(2-pyridyl) | 4-F | H | c-Pr | Et | 45–50 |

PNMR of Compound II-4 (CDCl₃) δppm: 1.24(t,J=9Hz,3H), 1.32(d,J=8Hz,6H0, 2.1–2.5(m,2H), 2.6–2.9(m,1H), 3.2–3.7(m,3H), 3.9–4.7(m,3H), PNMR of Compound II-5 (CDCl₃) δppm: 0.8–1.5(m,4H), 1.27(t,J=7Hz,3H), 1.89(s,3H), 2.1–2.4(m,1H), 2.51(d,J=6Hz,2H), 2.6–3.1(m,1H), 3.40(s,2H), 3.94(s,3H), 4.17(q,J=7Hz,2H), 4.4–4.8(m,1H), 5.3–5.7(m,1H), 6.4–6.8(m,1H), 7.0–7.4(m,4H)

PNMR of Compound II-10 (CDCl₃) δppm: 1.26(t,J=7Hz,3H), 1.33(d,J=7Hz,6H), 1.92(s,3H), 2.2–2.6(m,1H), 2.45(d,J=6Hz,2H), 3.41(s,2H), 3.43(Heptalet,J=7Hz,1H), 4.22(q,J=7Hz,2H), 4.4–4.8(m,1H), 4.8–5.6(m,1H), 5.65(s,2H), 6.4–6.8(m,1H), 7.0–7.7(m,9H)

PNMR of Compound II-14 (CDCl₃) δppm: 0.9–1.5(m,4H), 1.24(t,J=8Hz,3H), 2.1–2.5(m,1H), 2.5–2.7(m,2H), 3.31(s,2H), 4.05(s,3H), 4.12(q,J=8Hz,2H), 4.4–4.8(m,1H), 5.35(d,d,J=17Hz,J=6Hz,1H), 6.4–7.2(m,10H)

PNMR of Compound II-15 (CDCl₃) δppm: 0.9–1.4(m,4H), 1.26(t,J=8Hz,3H), 1.74(s,9H), 1.88(s,3H), 2.2–2.4(m,1H), 2.4–2.6(m,2H), 3.35(s,2H), 4.14(q,J=8Hz,2H), 4.3–4.7(m,1H), 5.40(d,d,J=17Hz,J=6Hz,1H), 6.50(d,J=17Hz,1H), 6.9–7.4(m,4H)

PNMR of Compound II-16 (CDCl₃) δppm: 0.4–1.4(m,8Hz), 1.28(t,J=8Hz,3H), 1.75(s,9H), 2.1–2.5(m,2H), 2.4–2.6(m,2H), 3.43(s,2H), 4.23(q,J=8Hz,2H), 4.4–4.7(m,1H), 5.52(d,d,J=17Hz,J=6Hz,1H), 6.64(d,1H,J=6Hz), 6.9–7.6(m,4H)

PNMR of Compound II-17 (CDCl₃) δppm: 0.8–1.5(m,4H), 1.20(t,J=8Hz,3H), 1.80(s,9H), 2.0–2.7(m,1H), 2.3–2.5(m,2H), 3.30(s,2H), 4.10(q,J=8Hz,2H), 4.3–4.7(m,1H), 5.35(d,d,J=17Hz,J=6Hz,1H), 6.3–7.3(m,10H)

In the same manner as in Example 1-g, Compounds I-1-2 to I-1-18 were prepared. Physical properties of the compounds thereby obtained are shown in the following Table.

TABLE 9

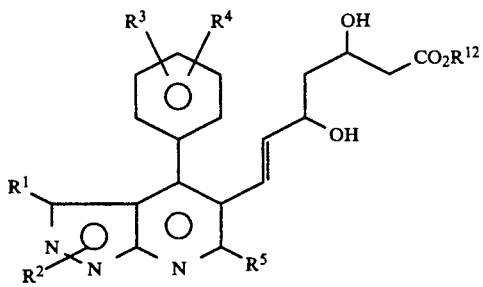

| Compound | $R^1$ | $R^2$ | $R^3$ | $R^4$ | $R^5$ | $R^{12}$ | Melting point (°C.) |
|---|---|---|---|---|---|---|---|
| I-1-2 | Me | 1-Ph | 4-F | H | i-Pr | Et | Oil |
| I-1-3 | Me | 2-Ph | 4-F | H | i-Pr | Et | Oil |
| I-1-4 | Ph | 1-Me | 4-F | H | i-Pr | Et | Oil |
| I-1-5 | Me | 1-Me | 4-F | H | c-Pr | Et | Oil |
| I-1-6 | H | 1-Ph | 4-F | H | i-Pr | Et | Oil |
| I-1-7 | Me | 1-t-Bu | 4-F | H | i-Pr | Et | Oil |
| I-1-8 | H | 1-Et | 4-F | H | i-Pr | Et | 58–63 |
| I-1-9 | c-Pr | 1-Me | 4-F | H | i-Pr | Et | 77–83 |
| I-1-10 | Me | 1-Ph—CH$_2$ | 4-F | H | i-Pr | Et | Oil |
| I-1-11 | 4-Cl—Ph | 1-Me | 4-F | H | i-Pr | Et | 116–120 |
| I-1-12 | c-Pr | 1-Ph | 4-F | H | i-Pr | Et | 99–102 |
| I-1-13 | Me | 1-(4-MeO—Ph) | 4-F | H | i-Pr | Et | 149–151 |
| I-1-14 | Ph | 1-Me | 4-F | H | c-Pr | Et | 45–50 |
| I-1-15 | Me | 1-t-Bu | 4-F | H | c-Pr | Et | 144–145 |
| I-1-16 | c-Pr | 1-t-Bu | 4-F | H | c-Pr | Et | 159–160 |
| I-1-17 | Ph | 1-t-Bu | 4-F | H | c-Pr | Et | 35–40 |
| I-1-18 | Me | 1-(2-pyridyl) | 4-F | H | c-Pr | Et | 35–38 |

PNMR of Compound I-1-2 (CDCl$_3$) δppm: 1.29(t,J=8Hz,3H), 1,36(d,J=8Hz,6H), 1.5–1.8(m,1H), 1.98(s,3H), 2.2–2.7(m,3H), 2.9–3.7(m,2H), 3.47(Heptalet,J=8Hz,1H), 3.8–4.6(m,2H), 4.20(q,J=8Hz,2H), 5.1–5.6(m,1H), 6.3–6.7(m,1H), 6.9–7.7(m,7H), 8.3–8.6(m,2H)

PNMR of Compound I-1-3 (CDCl$_3$) δppm: 1.1–1.5(m,9H), 1.6–1.7(m,1H), 1.9–2.0(m,3H), 2.3–2.5(m,2H), 2.8–3.2(m,1H), 3.3–3.7(m,3H), 3.8–4.5(m,4H), 5.2–5.6(m,1H), 6.4–6.7(m,1H), 7.0–7.6(m,7H), 8.3–8.5(m,2H)

PNMR of Compound I-1-4 (CDCl$_3$) δppm: 1.25(t,J=8Hz,3H), 1.33(d,J=8Hz,6H), 1.7–2.0(m,1H), 2.2–2.6(m,3H), 2.9–3.8(m,3H), 3.8–4.6(m,2H), 4.10(q,J=8Hz,2H), 4.12(s,3H), 4.9–5.4(m,1H), 6.3–7.2(m,10H)

PNMR of Compound I-1-5 (CDCl$_3$) δppm: 0.8–1.1(m,4H), 1.28(t,J=7Hz,3H), 1.4–1.8(m,2H), 1.89(s,3H), 2.1–2.6(m,4H), 3.0–3.8(m,2H), 3.98(s,3H), 4.18(q,J=7Hz,2H), 4.3–4.6(m,1H), 5.3–5.7(m,1H), 6.4–6.8(m,1H), 6.9–7.3(m,4H)

PNMR of Compound I-1-6 (CDCl$_3$) δppm: 1.29(t,J=7Hz,3H), 1.37(d,J=7Hz,6H), 1.4–1.9(m,2H), 2.2–4.7(m,2H), 3.0–3.9(m,3H), 3.9–4.7(m,2H), 4.19(q,J=7Hz,2H), 5.1–5.5(m,1H), 6.6–6.9(m,1H), 7.0–8.6(m,10H)

PNMR of Compound I-1-7 (CDCl$_3$) δppm: 1.28(t,J=7Hz,3H), 1.32(d,J=7Hz,6H), 1.4–1.8(m,2H), 1.84(s,9H), 1.89(s,3H), 2.3–2.6(m,3H), 3.1–3.7(m,1H), 3.41(Heptalet,J=7Hz,1H), 3.9–4.7(m,2H), 4.17(q,J=7Hz,2H), 5.1–5.5(m,1H), 6.4–6.7(m,1H), 6.9–7.3(m,4H)

PNMR of Compound I-1-10 (CDCl$_3$) δppm: 1.29(t,J=7Hz,3H), 1.33(d,J=7Hz,6H), 1.4–1.9(m,2H), 1.90(s,3H), 2.2–2.6(m,3H), 3.1–3.7(m,1H), 3.43(Heptalet,J=7Hz,1H), 3.8–4.5(m,2H), 4.19(q,J=7Hz,2H), 5.1–5.5(m,1H), 5.62(s,2H), 7.3–7.7(m,1H), 6.9–7.6(m,9H)

PNMR of Compound I-1-14 (CDCl$_3$) δppm: 0.9–1.3(m,4H), 1.4–1.8(m,2H), 1.28(t,J=8Hz,3H), 2.3–2.5(m,3H), 4.1–4.2(m,1H), 4.3–4.5(m,1H), 4.18(q,J=8Hz,2H), 4.13(s,3H), 5.45(d,d,J=17Hz,J=6Hz,1), 6.6–7.3(m,10H)

PNMR of Compound I-1-15 (CDCl$_3$) δppm: 0.9–1.4(m,4H), 1.29(t,J=8Hz,3H), 1.4–1.8(m,2H), 1.78(s,9H), 1.87(s,3H), 2.3–2.5(m,1H), 2.4–2.5(m,2H), 4.0–4.1(m,1H), 4.18(q,J=8Hz,2H), 4.3–4.4(m,1H), 5.50(d,d,J=17Hz,J=6Hz,1H), 6.55(d,J=17Hz,1H), 7.0–7.3(m,4H)

PNMR of Compound I-1-16 (CDCl3) δppm: 0.4–0.9(m,4H), 0.9–1.5(m,6H}, 1.29(t,J=8Hz,3H), 1.74(s,9H), 2.2–2.5(m,2H), 2.4–2.5(m,2H), 3.9–4.5(m,2H), 4.19(q,J=8Hz,2H), 5.50(d,d,J=17Hz,J=6Hz,1H), 6.58(d,J=17Hz,1H), 6.9–7.4(m,4H)

PNMR of Compound I-1-17 (CDCl$_3$) δppm: 0.9–1.5(m,6H), 1.28(t,J=8Hz,3H), 1.86(s,9H), 2.2–2.6(m,1H), 2.3–2.5(m,2H), 3.9–4.5(m,2H), 4.18(q,J=8Hz,2H), 5.45(d,d,J=17Hz,J=6Hz,1H), 6.63(d,J=17Hz,1H), 6.8–7.3(m,9H).

In the same manner as in Example 2, Compounds I-5-2 to I-5-18 were prepared. Physical properties of the compounds thereby obtained are shown in the following Table.

TABLE 10

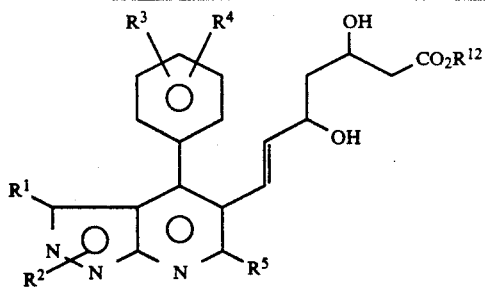

| Compound | R¹ | R² | R³ | R⁴ | R⁵ | R¹² | Melting point (°C.) |
|---|---|---|---|---|---|---|---|
| I-5-2 | Me | 1-Ph | 4-F | H | i-Pr | Na | 271–279 (Decomposed) |
| I-5-3 | Me | 2-Ph | 4-F | H | i-Pr | Na | 263–272 (Decomposed) |
| I-5-4 | Ph | 1-Me | 4-F | H | i-Pr | Na | 264–275 (Decomposed) |
| I-5-5 | Me | 1-Me | 4-F | H | c-Pr | Na | 230–237 (Decomposed) |
| I-5-6 | H | 1-Ph | 4-F | H | i-Pr | Na | 247–249 (Decomposed) |
| I-5-7 | Me | 1-t-Bu | 4-F | H | i-Pr | Na | 249–252 (Decomposed) |
| I-5-8 | H | 1-Et | 4-F | H | i-Pr | Na | — |
| I-5-9 | c-Pr | 1-Me | 4-F | H | i-Pr | Na | 215–220 (Decomposed) |
| I-5-10 | Me | 1-Ph—CH₂ | 4-F | H | i-Pr | Na | 240–247 (Decomposed) |
| I-5-11 | 4-Cl—Ph | 1-Me | 4-F | H | i-Pr | Na | 289–295 (Decomposed) |
| I-5-12 | c-Pr | 1-Ph | 4-F | H | i-Pr | Na | 207–214 (Decomposed) |
| I-5-13 | Me | 1-(4-MeO—Ph) | 4-F | H | i-Pr | Na | 220–226 (Decomposed) |
| I-5-14 | Ph | 1-Me | 4-F | H | c-Pr | Na | 240–250 (Decomposed) |
| I-5-15 | Me | 1-t-Bu | 4-F | H | c-Pr | Na | 225–230 (Decomposed) |
| I-5-16 | c-Pr | 1-t-Bu | 4-F | H | c-Pr | Na | 220–221 (Decomposed) |
| I-5-17 | Ph | 1-t-Bu | 4-F | H | c-Pr | Na | 210–215 (Decomposed) |
| I-5-18 | Me | 1-(2-pyridyl) | 4-F | H | c-Pr | Na | 160–175 (Decomposed) |

PNMR of Compound I-5-8 (CDCl₃) δppm: 1.0–1.7(m,2H), 1.29(d,J=7Hz,6H), 1.47(t,J=7Hz,3H), 1.7–2.3(m,3H), 3.1–3.3(m,1H), 3.3–3.9(m,1H), 3.53(Heptalet,J=7Hz,1H), 4.0–4.3(m,1H), 4.49(q,J=7Hz,2H), 5.2–5.5(m,1H), 6.4–6.7(m,1H), 7.0–7.7(m,5H)

PNMR of Compound I-5-14 (CDCl₃) δppm: 0.9–1.3(m,4H), 1.3–1.8(m,2H), 1.9–2.0(m,1H), 2.4–2.6(m,2H), 3.5–3.7(m,1H), 4.04(s,3H), 4.1–4.2(m,1H), 5.51(d,d,J=17Hz,J=6Hz,1H), 6.44(d,J=17Hz,1H), 6.8–7.2(m,9H)

PNMR of Compound I-5-15 (CDCl₃) δppm: 1.0–1.2(m,4H), 1.3–1.8(m,2H), 1.71(s,9H), 1.77(s,3H), 1.9–2.1(m,1H), 2.4–2.5(m,2H), 3.5–3.6(m,1H), 4.1–4.2(m,1H), 5.52(d,d,J=17Hz,J=6Hz,1H), 6.38(d,J=17Hz,1H), 7.1–7.3(m,4H)

PNMR of Compound I-5-16 (CDCl₃) δppm: 0.4–0.7(m,4H), 0.9–1.2(m,4H), 1.3–1.7(m,2H), 1.68(s,9H), 1.7–1.8(m,1H), 1.9–2.0(m,1H), 2.4–2.5(m,2H), 3.5–3.6(m,1H), 4.1–4.2(m,1H), 5.52(d,d,J=17Hz,J=6Hz,1H), 6.40(d,J=17Hz,1H), 7.2–7.4(m,4H)

PNMR of Compound I-5-17 (CDCl₃) δppm: 1.0–1.2(m,4H), 1.3–1.8(m,2H), 1.80(s,9H), 1.9–2.1(m,1H), 2.5–2.6(m,2H), 3.5–3.6(m,1H), 4.1–4.2(m,1H), 5.51(d,d,J=17Hz,J=6Hz,1H), 6.42(d,J=17Hz,1H), 6.8–7.2(m,9H)

EXAMPLE 3

(E)-7-[4'-(4''-fluorophenyl)-1',3'-dimethyl-6'-(1''-methylethyl)pyrazolo[3,4-b]pyridin-5'-yl]-3,5-dihydroxyhept-6-enoic acid (Compound I-2-1)

0.25 g (0.53 mmol) of Compound I-1 1 was dissolved in 3 ml of ethanol, and 1.06 ml of a 0.5 N sodium hydroxide aqueous solution was dripwise added thereto. Ethanol was distilled off under reduced pressure, and then, 3 ml of distilled water was added thereto. The solution was washed with diethyl ether. The aqueous layer was carefully neutralized with 1% hydrochloric acid and extracted with diethyl ether. The ether layer was dried over anhydrous magnesium sulfate and evaporated under reduced pressure to obtain the desired compound.

Quantity: 0.21 g (yield: 90%)

PNMR (DMSO-d⁶) δppm: 1.29(d,J=7Hz,6H), 1.83(s,3H), 2.1–2.3(m,2H), 2.4–2.6(m,1H), 3.0–3.6(m,4H), 3.96(s,3H), 4.3–4.8(m,2H), 5.2–5.6(m,1H), 6.3–6.6(m,1H), 7.2–7.4(m,4H), 11.5–12.0(bs,1H)

EXAMPLE 4

(E)-trans-6-(2'-[4''-(4'''-fluorophenyl)-1'',3''-dimethyl-6''-(1''-methylethyl)pyrazolo[3,4-b]pyridin-5''-yl]ethenyl)-4-hydroxy-3,4,5,6-tetrahydro-2H-pyran-2-one (Compound I-3-1)

130 mg (0.29 mmol) of Compound I-2-1 was dissolved in 6 ml of dichloromethane, and 125 mg (0.29 mmol) of N-cyclohexyl-N'-(2'-methylmorpholinoethyl)carbodiimide p-toluenesulfonate was added thereto. The mixture was stirred at room temperature for 2 hours and then subjected to distillation under reduced pressure to remove the solvent to dryness. The residual oil was purified by silica gel thin layer chromatography (eluent: hexane/ethyl acetate=9/1 (v/v)) to obtain the pure desired compound as colorless viscous oily substance.

Quantity: 48 mg (yield: 39%)

P-NMR (CDCl$_3$) $\delta$ppm: 1.33(d,J=6.8Hz,6H), 1.4–1.5(m,1H), 1.6–1.7(m,2H), 1.93(s,3H), 2.5–2.6(m,1H), 2.68(dd,J=18Hz,J=5Hz,1H), 3.39(Heptalet,J=6.8Hz,1H), 4.07(s,3H), 4.1–4.2(m,1H), 5.1–5.2(m,1H), 5.31(dd,J=16Hz,J=6Hz,1H), 6.61(dd,J=16Hz,J=1.5Hz,1H), 7.1–7.3(m,4H)

EXAMPLE 5

6-cyclopropyl-4-(4'-fluorophenyl)-5-hydroxymethyl-3-methyl-1-(2'-pyridyl)pyrazolo[3,4-b]pyridine (Compound VI-18) (Steps P, S and T)

5.04 g (1.25×10$^{-2}$ mol) of Compound VII-18 was dissolved in 50 ml of ethylene glycol, and 15 ml (1.5×10$^{-2}$ mol) of a 1 mol/l sodium hydroxide aqueous solution was added thereto. The reaction solution was stirred at 220° C. for three days. After confirming the disappearance of the starting material by thin layer chromatography, the reaction solution was cooled to room temperature. Chloroform, a sodium chloride aqueous solution and diluted hydrochloric acid were added to the reaction solution to adjust pH to 2. The product was extracted with chloroform. The chloroform layer was washed with water and dried over anhydrous magnesium sulfate. The solvent was distilled off to obtain colorless powdery crystals. The powdery crystals were thoroughly washed with n-hexane to obtain 4.60 g (Yield: 94.8%) of Compound XIII 18.

Melting point: 235°–245° C.

4.24 g (1.09×10$^{-2}$ mol) of Compound XIII-18 was suspended in 90 ml of dry benzene. 6.92 g (5.45×10$^{-2}$ mol) of oxalyl dichloride was added thereto, and the mixture was heated and stirred at 60° C. Four hours later, 3 g of oxalyl dichloride was further added thereto, and the heating and stirring were continued for 4 hours. After confirming the disappearance of the starting material by thin layer chromatography, the solvent was distilled off by an evaporator to obtain Compound XIV-18 as slightly yellow powder. Compound XIV-18 thereby obtained was dissolved in 90 ml of dry diethyl ether without purification. 0.78 g (2.06×10$^{-2}$ mol) of lithium aluminum hydride was added thereto, and the mixture was stirred at room temperature for 5 hours. After confirming the disappearance of the starting material by thin layer chromatography, chloroform, ice and an ammonium chloride aqueous solution were added thereto to terminate the reaction. The product was extracted with chloroform. The chloroform layer was washed with a diluted sodium hydroxide aqueous solution and with a sodium chloride aqueous solution and dried over anhydrous magnesium sulfate. Then, the solvent was evaporated. The residue thereby obtained was purified by silica gel column chromatography (eluent: benzene/ethyl acetate) to obtain 3.27 g (Yield: 80.2% based on Compound XIII-18) of the desired Compound VI-18 as slightly yellow powder.

Melting point: 75°–82° C.

FORMULATION EXAMPLE 1

| Tablets | |
|---|---|
| Compound I-5-1 | 1.0 g |
| Lactose | 5.0 g |
| Crystal cellulose powder | 8.0 g |
| Corn starch | 3.0 g |
| Hydroxypropyl cellulose | 1.0 g |
| CMC—Ca | 1.5 g |
| Magnesium stearate | 0.5 g |
| Total | 20.0 g |

The above components were mixed by a usual method and then tabletted to produce 100 tablets each containing 10 mg of the active ingredient.

FORMULATION EXAMPLE 2

| Capsules | |
|---|---|
| Compound I-5-1 | 1.0 g |
| Lactose | 3.5 g |
| Crystal cellulose powder | 10.0 g |
| Magnesium stearate | 0.5 g |
| Total | 15.0 g |

The above components were mixed by a usual method and then packed in No. 4 gelatin capsules to obtain 100 capsules each containing 10 mg of the active ingredient.

FORMULATION EXAMPLE 3

| Soft capsules | |
|---|---|
| Compound I-5-1 | 1.00 g |
| PEG (polyethylene glycol) 400 | 3.89 g |
| Saturated fatty acid triglyceride | 15.00 g |
| Peppermint oil | 0.01 g |
| Polysorbate 80 | 0.10 g |
| Total | 20.00 g |

The above components were mixed and packed in No. 3 soft gelatin capsules by a usual method to obtain 100 soft capsules each containing 10 mg of the active ingredient.

FORMULATION EXAMPLE 4

| Ointment | | |
|---|---|---|
| Compound I-5-1 | 1.0 g | (10.0 g) |
| Liquid Paraffin | 10.0 g | (10.0 g) |
| Cetanol | 20.0 g | (20.0 g) |
| White vaseline | 68.4 g | (59.4 g) |
| Ethylparaben | 0.1 g | (0.1 g) |
| l-menthol | 0.5 g | (0.5 g) |
| Total | 100.0 g | |

The above components were mixed by a usual method to obtain a 1% (10%) ointment.

FORMULATION EXAMPLE 5

| Suppository | |
|---|---|
| Compound I-5-1 | 1.0 g |
| Witepsol H15* | 46.9 g |
| Witepsol W35* | 52.0 g |
| Polysorbate 80 | 0.1 g |
| Total | 100.0 g |

*Trademark for triglyceride compound

The above components were melt-mixed by a usual method and poured into supository containers, followed by cooling for solidification to obtain 100 suppositories of 1 g each containing 10 mg of the active ingredient.

FORMULATION EXAMPLE 6

| Injection formulation | |
|---|---|
| Compound I-5-1 | 1 mg |
| Distilled water for injection formulation | 5 ml |

The formulation is prepared by dissolving the compound in the distilled water whenever it is required.

FORMULATION EXAMPLE 7

| Granules | |
|---|---|
| Compound I-5-1 | 1.0 g |
| Lactose | 6.0 g |
| Crystal cellulose powder | 6.5 g |
| Corn starch | 5.0 g |
| Hydroxypropyl cellulose | 1.0 g |
| Magnesium stearate | 0.5 g |
| Total | 20.0 g |

The above components were granulated by a usual method and packaged to obtain 100 packages each containing 200 mg of the granules so that each package contains 10 mg of the active ingredient.

We claim:

1. A compound of the formula:

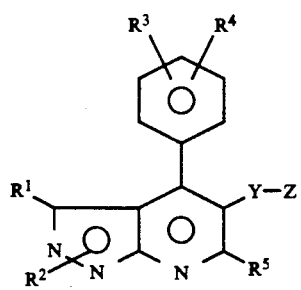

(I)

wherein $R^2$ is hydrogen, $C_{1-8}$ alkyl, $C_{1-6}$ alkoxy, $C_{3-7}$ cycloalkyl, $C_{2-6}$ alkenyl, α-or β-naphthyl, 2-, 3- or 4-pyridyl, 2- or 3-thienyl, 2- or 3-furyl, fluoro, chloro, bromo,

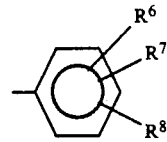

(wherein $R^6$, $R^7$ and $R^8$ are independently hydrogen, $C_{1-8}$ alkyl, $C_{1-8}$ alkoxy, $C_{1-3}$ alkylthio, chloro, bromo, fluoro, —$NR^9R^{10}$ (wherein $R^9$ and $R^{10}$ are independently $C_{1-3}$ alkyl), chloromethyl, trichloromethyl, trifluoromethyl, trifluoromethoxy, trichloromethoxy, difluoromethoxy, phenoxy, benzyloxy, hydroxy, trimethylsilyloxy, diphenyl-t-butylsilyloxy, hydroxymethyl or —$O(CH_2)_kOR^{18}$ (wherein $R^{18}$ is hydrogen or $C_{1-3}$ alkyl, and k is 1, 2 or 3); when $R^8$ is hydrogen and when located at the ortho position to each other, $R^6$ and $R^7$ may together form —$OC(R^{19})(R^{20})O$— wherein $R^{19}$ and $R^{20}$ are independently hydrogen or $C_{1-3}$ alkyl); or when $R^7$ and $R^8$ are hydrogen at the same time, $R^6$ is

(wherein $R^{25}$ is hydrogen, $C_{1-4}$ alkyl, $C_{1-3}$ alkoxy, trifluoromethyl, chloro, bromo, or fluoro)), phenyl-$C_{2-3}$ alkenyl of which the phenyl group is unsubstituted or substituted by $C_{1-4}$ alkyl, $C_{1-3}$ alkoxy, fluorine, chlorine or bromine, or $C_{1-3}$ alkyl substituted by one member selected from the group consisting of $C_{1-3}$ alkoxy, naphthyl and

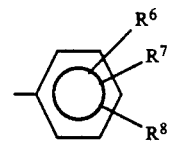

(wherein $R^6$, $R^7$ and $R^8$ are as defined above); $R^2$ is bonded to nitrogen at the 1- or 2-position of the pyrazolopyridine ring and is hydrogen, $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl, 2- or 3-thienyl, 2- or 3-furyl or

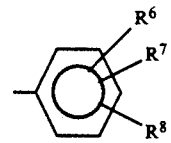

(wherein $R^6$, $R^7$ and $R^8$ are as defined above), or $C_{1-3}$ alkyl substituted by one member selected from the group consisting of $C_{1-3}$ alkoxy, hydroxy, naphthyl and

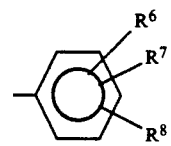

(wherein R⁶, R⁷ and R⁸ are as defined above) R³ and R⁴ are independently hydrogen, $C_{1-8}$ alkyl, $C_{3-7}$ cycloalkyl, $C_{1-3}$ alkoxy, n-butoxy, i-butoxy, sec-butoxy, $R^{23}R^{24}N-$ (wherein $R^{23}$ and $R^{24}$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{15}$ (wherein $R^{15}$ is hydrogen or $C_{1-3}$ alkyl, and l is 1, 2 or 3); or when located at the ortho position to each other, R³ and R⁴ may together form —CH=CH—CH=CH— or methylene dioxy; Y is —CH₂—, —CH₂CH₂—, —CH=CH—, —CH₂—CH=CH—, —CH=CH—CH₂—, —C(CH₃)=CH— or —CH=C(CH₃); Z is —Q—CH₂WCH₂—CO₂R¹²,

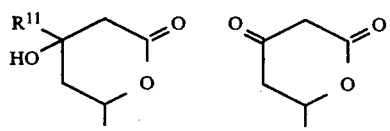

or

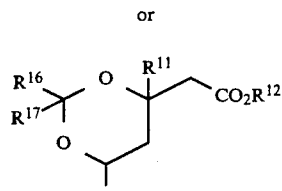

(wherein Q is —C(O)—, —C(OR¹³)₂— or —CH(OH)—; W is —C(O)—, —C(OR¹³)₂— or —C(R¹¹)(OH)—; R¹¹ is hydrogen or $C_{1-3}$ alkyl; R¹² is hydrogen or R¹⁴ (wherein R¹⁴ is alkyl moiety of chemically or physiologically hydrolyzable alkyl ester or M (wherein M is NH₄, sodium, potassium, ½ calcium or a hydrogen addition product to nitrogen of lower alkylamine, di-lower alkylamine or tri-lower alkylamine)): two R¹³ are independently primary or secondary $C_{1-6}$ alkyl; or two R¹³ together form —(CH₂)₂ or —(CH₂)₃—; R¹⁶ and R¹⁷ are independently hydrogen or $C_{1-3}$ alkyl; or R¹⁶ and R¹⁷ together form —(CH₂)₂— or —(CH₂)₃—; and R⁵ is cyclopropyl.

2. The compound according to claim 1, wherein in the formula I, when R⁴ is hydrogen, R³ is hydrogen, 3-fluoro, 3-chloro, 3-methyl, 4-methyl, 4-chloro or 4-fluoro; or R³ and R⁴ together represent 3-methyl-4-chloro, 3,5-dichloro, 3,5-difluoro, 3,5-dimethyl or 3-methyl-4-fluoro; R⁵ is cyclopropyl; Y is —CH₂—CH₂— or —CH=CH—; and Z is

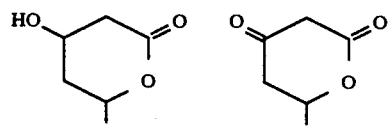

—CH(OH)CH₂CH(OH)CH₂CO₂R¹², —CH(OH)CH₂C(O)CH₂CO₂R¹² or —CH(OH)CH₂C(OR¹³)₂CH₂CO₂R¹² (wherein R¹² and R¹³ are as defined above).

3. The compound according to claim 2, wherein in the formula I, R¹ is hydrogen, $C_{1-8}$ alkyl, $C_{16}$ alkoxy, $C_{3-7}$ cycloalkyl, $C_{2-6}$ alkenyl, α- or β-naphthyl, 2-, 3- or 4-pyridyl, 2- or 3-thienyl, 2- or 3-furyl,

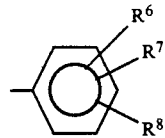

$C_{1-3}$ alkyl substituted by one member selected from the group consisting of $C_{1-3}$ alkoxy, naphthyl and

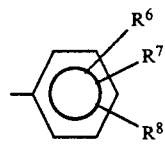

R² is bonded to nitrogen at the 1- or 2-position of the pyrazolopyridine ring and R² is $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl, or

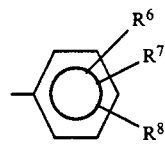

(wherein R⁶, R⁷ and R⁸ are as defined above), or $C_{1-3}$ alkyl substituted by one member selected from the group consisting of $C_{1-3}$ alkoxy, hydroxy, naphthyl and

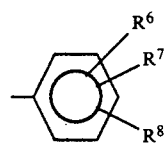

when R⁴ is hydrogen; R³ is hydrogen, 4-methyl, 4-chloro or 4-fluoro; or R³ and R⁴ together form 3,5-dimethyl or 3-methyl-4-fluoro; and Y is —CH₂—CH₂— or (E)-CH=CH—.

4. The compound according to claim 2, wherein in the formula I, R¹ is hydrogen, $C_{1-8}$ alkyl, $C_{3-7}$ cycloalkyl, $C_{2-6}$ alkenyl or

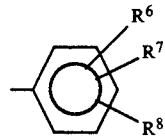

when R² is bonded to nitrogen at the 1-position of the pyrazolopyridine ring, R² is $C_{1-8}$ alkyl, $C_{1-3}$ alkyl substituted by 1 to 3 fluorine, $C_{3-7}$ cycloalkyl, α- or β-naphthyl, 2-, 3- or 4-pyridyl, or

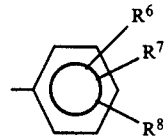

or C$_{1-3}$ alkyl substituted by one member selected from the group consisting of C$_{1-3}$ alkoxy, hydroxy, naphthyl and

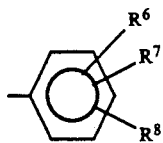

or when R$^2$ is bonded to nitrogen at the 2-position of the pyrazolopyridine ring, R$^2$ is α- or β-naphthyl or

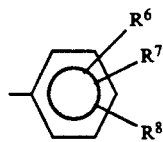

(wherein R$^6$, R$^7$ and R$^8$ are as defined above); when R$^4$ is hydrogen; and R$^3$ is hydrogen, 4-chloro or 4-fluoro; or R$^4$ and R$^3$ together form 3-methyl-4-fluoro; R$^5$ is cyclopropyl; and Y is (E)--CH=CH--.

5. The compound according to claim 2, wherein in the formula I, R$^1$ is hydrogen, methyl, ethyl, n-propyl, i-propyl, n-butyl, i-butyl, sec-butyl, t-butyl, cyclopropyl, cyclohexyl, phenyl, 2-, 3- or 4-fluorophenyl, 2-, 3- or 4-chlorophenyl, 2-, 3- or 4-bromopheny, 2-, 3- or 4-tolyl, 2-, 3- or 4-methoxyphenyl, 2-, 3- or 4-trifluoromethylphenyl, 2-, 3- or 4-chloromethylphenyl, 3- or 4-ethoxyphenyl, 4-(2-methylbutyl)phenyl, 4-n-heptylphenyl, 4-n-octylphenyl, 4-n-pentylphenyl, 4-n-hexylphenyl, 4-n-propylphenyl, 4-n-butylphenyl, 4-t-butylphenyl, 4-n-butoxyphenyl, 4-n-pentyloxyphenyl, 4-n-hexyloxyphenyl, 4-n-heptyloxyphenyl 4-n-octyloxyphenyl, 4-phenoxyphenyl, 4-biphenyl, 4-trichloromethoxyphenyl, 2,4-difluorophenyl, 2,6-difluorophenyl, 2,3-difluorophenyl, 3,5-difluorophenyl, 2,5-difluorophenyl, 3,4-difluorophenyl, 2,4-dichlorophenyl, 2,6 dichlorophenyl, 2,3-dichlorophenyl 2,5-dichlorophenyl, 3,5-dichlorophenyl, 3,4-dichlorophenyl, 2,3-dimethylphenyl, 2,5-dimethylphenyl, 2,6-dimethylphenyl, 3,4-dimethylphenyl, 2,5-dimethoxyphenyl, 2,6-dimethoxyphenyl, 2,4-dimethoxyphenyl, 3,4-dimethoxyphenyl, 3,5-dimethoxyphenyl, 3,5-bis(trifluoromethyl)phenyl, 3,4-methylenedioxyphenyl, 2,4,6-trimethoxyphenyl, 3,4,5-trimethylphenyl, or 2,4,6-tirisopropylphenyl; R$^2$ is bonded to nitrogen at the 1-position of the pyrazolopyridine ring and is methyl, ethyl, n-propyl, i-propyl, n-butyl, i-butyl, sec-butyl, t-butyl, 2,2,2-trifluoroethyl, 2-hydroxyethyl, cyclohexyl, benzyl, 2-chlorobenzyl, 2-hydroxybenzyl, 3-trifluoromethylbenzyl, 2-phenylethyl, phenyl, 2-, 3- or 4-chlorophenyl, 2-, 3- or 4-bromophenyl, 2-, 3- or 4-fluorophenyl, 2-, 3- or 4-tolyl, 2-, 3- or 4-trifluoromethylphenyl, 3- or 4-methoxyphenyl, 2-hydroxyphenyl, 4-isopropylphenyl, 4-t-butylphenyl, 4-trifluoromethoxyphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2,3,4-trichlorophenyl, 2,4-difluorophenyl, 3,5-bis(trifluoromethyl)phenyl, 3-chloro-4-tolyl, 3-chloro-6-tolyl, 4-chloro-2-tolyl, 2-chloro-6 tolyl, 2-chloro-6-fluorophenyl, 2-chloro-5-trifluoromethylphenyl, 3-chloro-4-fluorophenyl, 4-bromo-3-chlorophenyl, 2-chloro-4-trifluoromethylphenyl, 3-fluoro-6-tolyl, α-naphthyl, 2-pyridyl, 3-methyl-5-trifluoromethyl-2-pyridyl, 4-pyridyl or 2,6-dichloro-4-pyridyl; R$^3$ is hydrogen, R$^4$ is 4-chloro or 4-fluoro; R$^5$ is cyclopropyl; and Y is (E)--CH=CH--.

6. The compound according to claim 1, which is (E)-3,5-dihydroxy-7-[6'-cyclopropyl-4'-(4''-fluorophenyl)-1',3'-dimethylpyrazolo[3,4-b]pyridin-5'-yl]hept-6-enoic acid, a lactone formed by the condensation of the carboxylic acid with hydroxy at the 5 position, or a sodium salt or C$_{1-3}$ alkyl ester of the carboxylic acid.

7. The compound according to claim 1, which is (E)-3,5-dihydroxy-7-[1'-t-butyl-6'-cyclopropyl-4'-(4''-fluorophenyl)-3'-methylpyrazolo[3,4-b]pyridin-5'-yl]-hept-6-enoic acid, a lactone formed by the condensation of the carboxylic acid with hydroxy at the 5-position, or a sodium salt or C$_{1-3}$ alkyl ester of the carboxylic acid.

8. The compound according to claim 1, which is (E)-3,5-dihydroxy-7-[1'-benzyl-6'-cyclopropyl-4'-(4''-fluorophenyl)-3'-methylpyrazolo[3,4-b]pyridin-5'-yl]-hept-6-enoic acid, a lactone formed by the condensation of the carboxylic acid with hydroxy at the 5-position, or a sodium salt or Cl-3 alkyl ester of the carboxylic acid.

9. The compound according to claim 1, which is (E)-3,5-dihydroxy-7-[6'-cyclopropyl-4'-(4''-fluorophenyl)-1'-(4''-methoxyphenyl)-3'-methylpyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

10. The compound according to claim 1, which is (E)-3,5-dihydroxy-7-[3',6'-dicyclopropyl-4'-(4''-fluorophenyl)-1'-methylpyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

11. The compound according to claim 1, which is (E)-3,5-dihydroxy-7-[6'-cyclopropyl-4'-(4''-fluorophenyl)-1'-methyl-3'-phenylpyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

12. The compound according to claim 1, which is (E)-3,5-dihydroxy-7-[3'-(4''-chlorophenyl)-6'-cyclopropyl-4'-(4'''-fluorophenyl)-1'-methylpyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

13. The compound according to claim 1, which is (E)-3,5-dihydroxy-7-[6'-cyclopropyl-1'-ethyl-4'-(4''-fluorophenyl)pyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

14. The compound according to claim 1, which is (E)-3,5-dihydroxy-7-[6'-cyclopropyl-4'-(4''-fluorophenyl)-1'-phenylpyrazolo[3,4-b]pyridin-5'-yl]hept-6-enoic acid, a lactone formed by the condensation of the carboxylic acid with hydroxy at the 5-position, or a sodium salt or C$_{1-3}$ alkyl ester of the carboxylic acid.

15. The compound according to claim 1, which is (E)-3,5-dihydroxy-7-[6'-cyclopropyl-4'-(4''-fluorophenyl)-3'-methyl-1'-phenylpyrazolo[3,4-b]pyridin-5'-yl]hept-6-enoic acid, a lactone formed by the condensation of the carboxylic acid with hydroxy at the 5-position, or a sodium salt or $C_{1-3}$ alkyl ester of the carboxylic acid.

16. The compound according to claim 1, which is (E)-3,5-dihydroxy-7-[3',6'-dicyclopropyl-4'-(4''-fluorophenyl)-1'-phenylpyrazolo[3,4-b]pyridin-5'-yl]hept-6-enoic acid, a lactone formed by the condensation of the carboxylic acid with hydroxy at the 5-position, or a sodium salt or $C_{1-3}$ alkyl ester Of the carboxylic acid.

17. The compound according to claim 1, which is (E)-3,5-dihydroxy-7-[1'-t-butyl-3',6'-dicyclopropyl-4'-(4''-fluorophenyl)pyrazolo[3,4-b]pyridin-5'-yl]hept-6-enoic acid, a lactone formed by the condensation of the carboxylic acid with hydroxy at the 5-position, or a sodium salt or $C_{1-3}$ alkyl ester of the carboxylic acid.

18. The compound according to claim 1, which is (E)-3,5-dihydroxy-7-[1'-t-butyl-6'-cyclopropyl-4'-(4''-fluorophenyl)-3'-phenylpyrazolo[3,4-b]pyridin-5'-yl]hept-6-enoic acid, a lactone formed by the condensation of the carboxylic acid with hydroxy at the 5-position, or a sodium salt or $C_{1-3}$ alkyl ester of the carboxylic acid.

19. An anti-hyperlipidemia agent containing the compound of the formula I-1 as defined in claim 1 in a pharmaceutically acceptable inert diluent.

20. An anti-hyperlipoproteinemia agent containing the compound of the formula I as defined in claim 1 in a pharmaceutically acceptable inert diluent.

21. An anti-atherosclerosis agent containing the compound of the formula I as defined in claim 1 in a pharmaceutically acceptable inert diluent.

22. A method for reducing hyperlipidemia, hyperlipoproteinemia or atherosclerosis, which comprises administering an effective amount of the compound of the formula I as defined in claim 1.

* * * * *

UNITED STATES PATENT AND TRADEMARK OFFICE
CERTIFICATE OF CORRECTION

PATENT NO. : 5,024,999
DATED : June 18, 1991
INVENTOR(S) : Yoshihiro Fujikawa et al.

It is certified that error appears in the above-identified patent and that said Letters Patent is hereby corrected as shown below:

ON THE TITLE PAGE:

The title is incorrect, should be, --PYRAZOLOPYRIDINE TYPE MEVALONOLACTONES USEFUL AS PHARMACEUTICALS--, and the last inventor's name is spelled incorrectly, should be, --Masaki Kitahara--.

Signed and Sealed this

Tenth Day of November, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 5,024,999

DATED : JUNE 18, 1991

INVENTOR(S) : YOSHIHIRO FUJIKAWA, et al

It is certified that error appears in the above-identified patent and that said Letters Patent is hereby corrected as shown below:

Column 45, line 65, correct "$R^2$" to read --$R^1$--;

Column 47, line 1, correct ") $R^{3'}$ to read --); $R^3$--;

Column 47, line 66, correct "$C_{16}$" to read --$C_{1-6}$--;

Column 49, line 29, correct "4-bromopheny" to read -- 4-bromophenyl;

Column 49, line 40, correct "2,6 dichlo-" to read --2,6-dichlo- --;

Column 49, line 64, correct "2-chloro-6 tolyl," to read --2-chloro-6-tolyl,--;

Column 50, line 5, correct

"(E)-3,5-dihydroxy-7-[6'-cyclopropyl-4'-4'-fluoro-" to read --(E)-3,5-dihydroxy-7-[6'-cyclopropyl-4'-4"-fluoro-"--;

Column 50, line 22, correct "CI-3" to read --$C_{1-3}$--;

Column 50, line 65, correct "(E)}" to read --(E)--;

Column 51, line 8, correct "Of" to read --of--; and

UNITED STATES PATENT AND TRADEMARK OFFICE
CERTIFICATE OF CORRECTION

PATENT NO. : 5,024,999

DATED : JUNE 18, 1991

INVENTOR(S) : YOSHIHIRO FUJIKAWA, et al

It is certified that error appears in the above-identified patent and that said Letters Patent is hereby corrected as shown below:

Column 52, line 5, correct "formula I-1" to read --formula I--.

Signed and Sealed this

Twentieth Day of July, 1993

*Attest:*

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO. : 5,024,999

DATED : June 18, 1991

INVENTOR(S) : YOSHIHIRO FUJIKAWA ET AL

It is certified that error appears in the above-identified patent and that said Letters Patent is hereby corrected as shown below:

Column 29, line 49, change "Relative" to --Inhibitory--.

Signed and Sealed this

Ninth Day of November, 1993

Attest:

BRUCE LEHMAN

*Attesting Officer*          *Commissioner of Patents and Trademarks*